(12) United States Patent
Tomita et al.

(10) Patent No.: US 12,428,453 B2
(45) Date of Patent: Sep. 30, 2025

(54) MODIFIED CHANNELRHODOPSIN

(71) Applicant: NATIONAL UNIVERSITY CORPORATION, IWATE UNIVERSITY, Morioka (JP)

(72) Inventors: Hiroshi Tomita, Morioka (JP); Eriko Sugano, Morioka (JP)

(73) Assignee: NATIONAL UNIVERSITY CORPORATION, IWATE UNIVERSITY, Morioka (JP)

(*) Notice: Subject to any disclaimer, the term of this patent is extended or adjusted under 35 U.S.C. 154(b) by 567 days.

(21) Appl. No.: 17/913,749

(22) PCT Filed: Mar. 24, 2021

(86) PCT No.: PCT/JP2021/012282
§ 371 (c)(1),
(2) Date: Dec. 5, 2022

(87) PCT Pub. No.: WO2021/193731
PCT Pub. Date: Sep. 30, 2021

(65) Prior Publication Data
US 2023/0331790 A1    Oct. 19, 2023

(30) Foreign Application Priority Data

Mar. 24, 2020 (JP) .................. 2020-053473

(51) Int. Cl.
*C07K 14/405* (2006.01)
*A61P 27/02* (2006.01)
*C12N 15/63* (2006.01)

(52) U.S. Cl.
CPC ............ *C07K 14/405* (2013.01); *A61P 27/02* (2018.01); *C12N 15/63* (2013.01); *C07K 2319/03* (2013.01)

(58) Field of Classification Search
None
See application file for complete search history.

(56) References Cited

U.S. PATENT DOCUMENTS

| 2012/0190629 A1 | 7/2012 | Tomita |
| 2013/0066402 A1 | 3/2013 | Lin |
| 2016/0002302 A1 | 1/2016 | Deisseroth |

FOREIGN PATENT DOCUMENTS

| EP | 3854876 A1 | 7/2021 |
| JP | 2014-500716 A | 1/2014 |
| WO | 2011/019081 A1 | 2/2011 |
| WO | 2012/061676 A1 | 5/2012 |
| WO | 2020/059675 A1 | 3/2020 |

OTHER PUBLICATIONS

International Search Report for International Application No. PCT/JP2021/012282 dated Jun. 15, 2021 (2 sheets).
Extended European Search Report for corresponding European Patent Application No. 21775203.9 issued Feb. 6, 2024 (12 sheets).
O. Yizhar, et al.; "Neocortical excitation/inhibition balance in information processing and social dysfunction"; Nature; Sep. 5, 2014; 477(7364); DOI:10.1038/nature10360; pp. 1-21 (21 pages).
O. Yizhar, et al.; "Supplementary Figures to: Neocortical excitation/inhibition balance in information processing and social dysfunction"; Nature; Sep. 5, 2014; DOI:10.1038/nature10360; pp. 1-33 (33 pages).

*Primary Examiner* — Brian Gangle
(74) *Attorney, Agent, or Firm* — Kratz, Quintos & Hanson, LLP

(57) ABSTRACT

An object of the present invention is to provide a modified channelrhodopsin having high ion permeability (photoreactivity). The solution is to substitute the third extracellular domain counted from the N-terminal side of three extracellular domains included in a *Volvox carteri*-derived channelrhodopsin by a corresponding extracellular domain of a *Chlamydomonas reinhardtii*-derived channelrhodopsin-2.

21 Claims, 4 Drawing Sheets
Specification includes a Sequence Listing.

[FIG. 1]
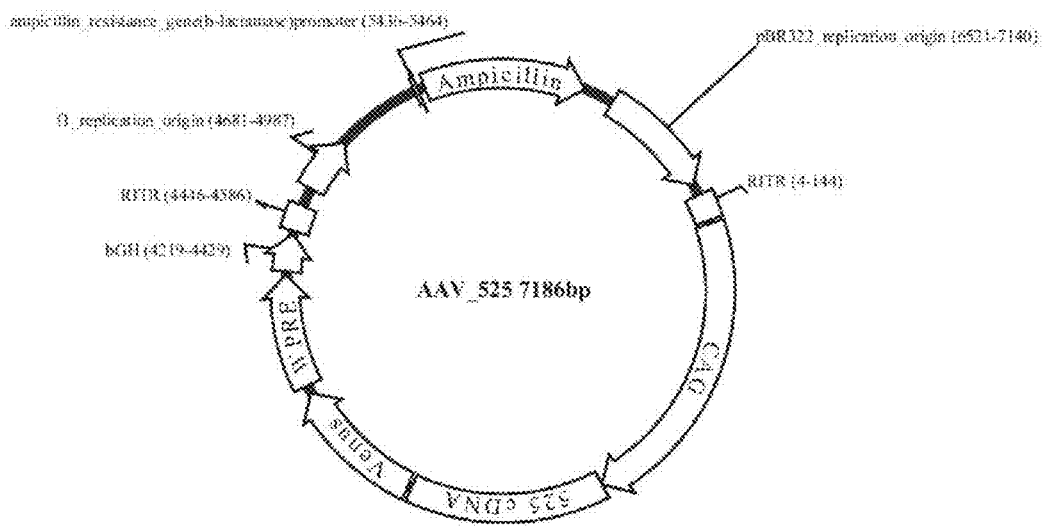
[FIG. 2]
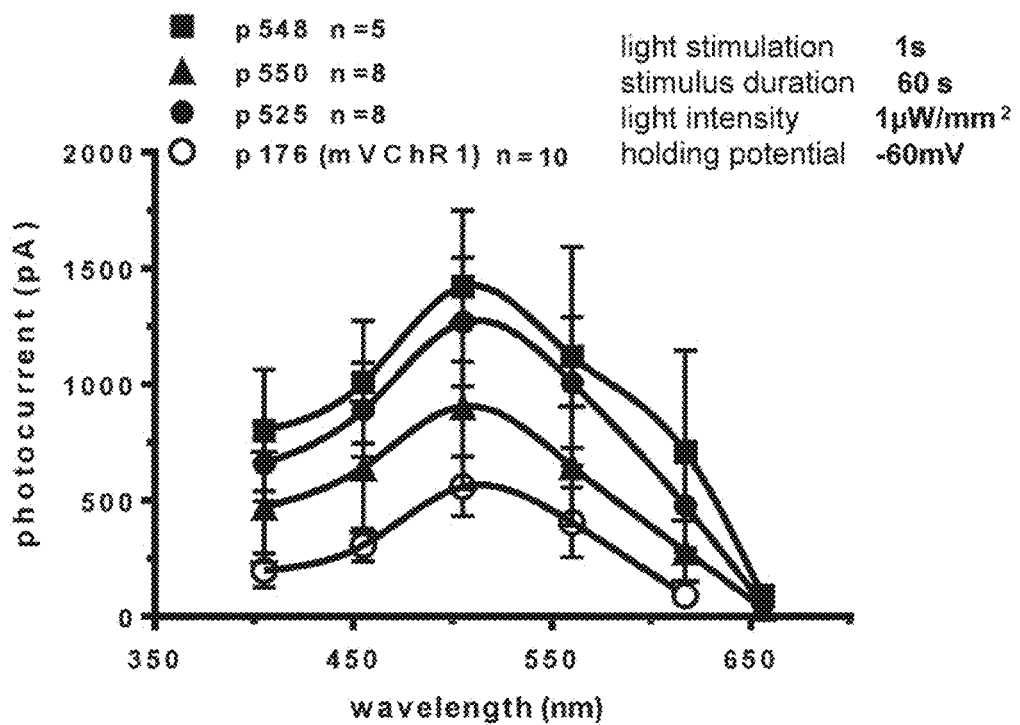

[FIG. 3]
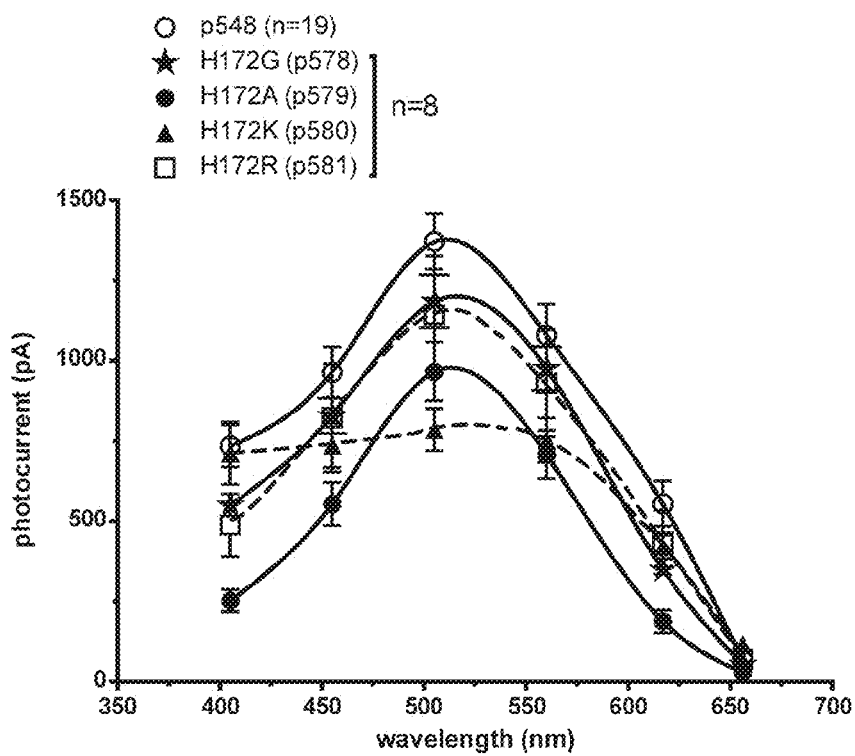
[FIG. 4]
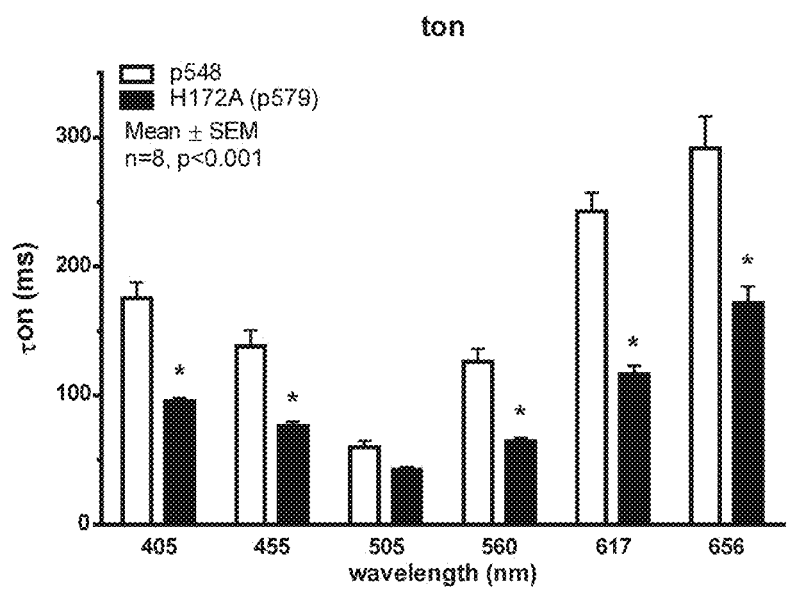

[FIG. 5]
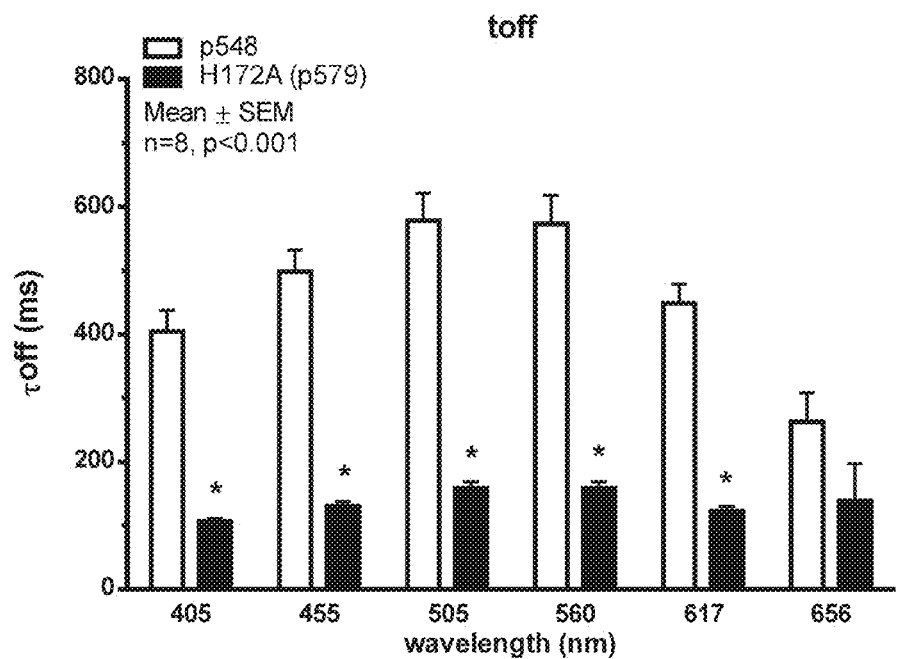
[FIG. 6]
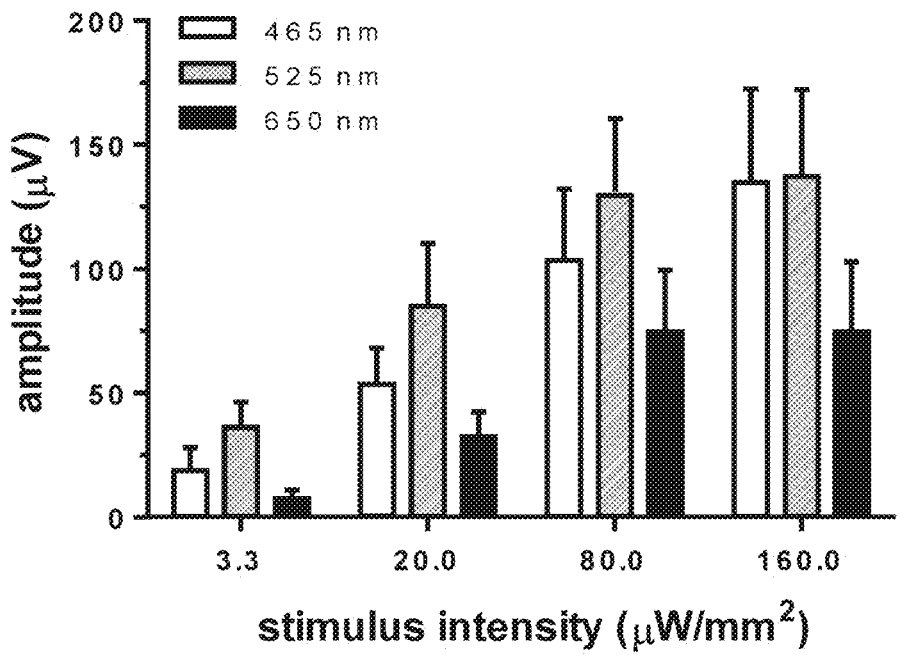

[FIG. 7]
[FIG. 8]
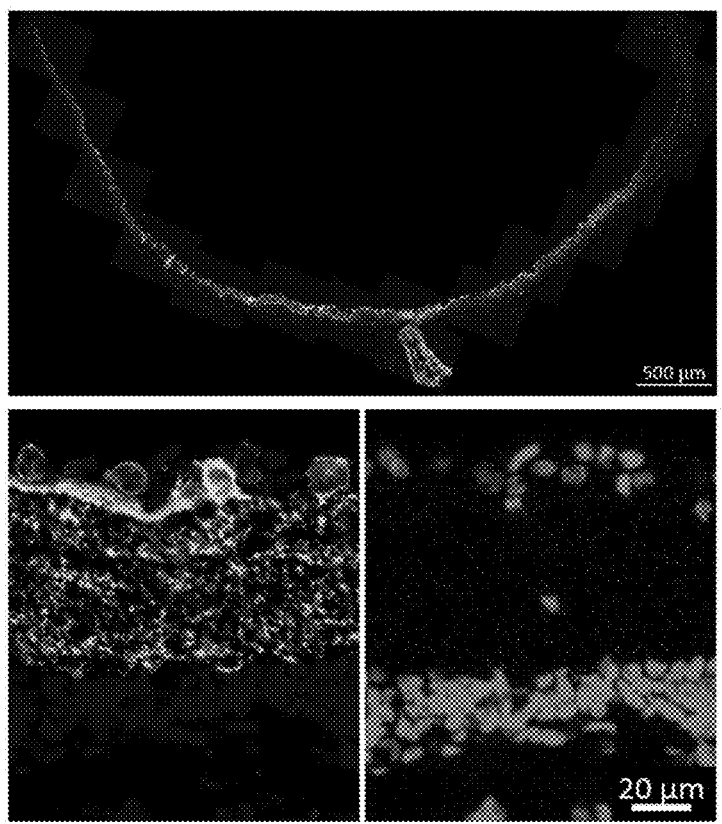

SEQUENCE LISTING

<160> NUMBER OF SEQ ID NOS: 25

<210> SEQ ID NO 1
<211> LENGTH: 344
<212> TYPE: PRT
<213> ORGANISM: Artificial Sequence
<220> FEATURE:
<223> OTHER INFORMATION: Fusion protein, mVChR1

<400> SEQUENCE: 1

Met Ser Arg Arg Pro Trp Leu Leu Ala Leu Ala Leu Ala Val Ala Leu
1               5                   10                  15

Ala Ala Gly Ser Ala Gly Ala Ser Thr Gly Ser Asp Ala Thr Val Pro
            20                  25                  30

Val Ala Thr Gln Asp Gly Pro Asp Tyr Val Phe His Arg Ala His Glu
        35                  40                  45

Arg Met Leu Phe Gln Thr Ser Tyr Thr Leu Glu Asn Asn Gly Ser Val
    50                  55                  60

Ile Cys Met Pro Arg Gly Gln Cys Tyr Cys Glu Gly Trp Leu Arg Ser
65                  70                  75                  80

Arg Gly Thr Ser Ile Glu Lys Thr Ile Ala Ile Thr Leu Gln Trp Val
                85                  90                  95

Val Phe Ala Leu Ser Val Ala Cys Leu Gly Trp Tyr Ala Tyr Gln Ala
            100                 105                 110

Trp Arg Ala Thr Cys Gly Trp Glu Glu Val Tyr Val Ala Leu Ile Glu
        115                 120                 125

Met Met Lys Ser Ile Ile Glu Ala Phe His Glu Phe Asp Ser Pro Ala
    130                 135                 140

Thr Leu Trp Leu Ser Ser Gly Asn Gly Val Val Trp Met Arg Tyr Gly
145                 150                 155                 160

Glu Trp Leu Leu Thr Cys Pro Val Leu Leu Ile His Leu Ser Asn Leu
                165                 170                 175

Thr Gly Leu Lys Asp Asp Tyr Ser Lys Arg Thr Met Gly Leu Leu Val
            180                 185                 190

Ser Asp Val Gly Cys Ile Val Trp Gly Ala Thr Ser Ala Met Cys Thr
        195                 200                 205

Gly Trp Thr Lys Ile Leu Phe Phe Leu Ile Ser Leu Ser Tyr Gly Met
    210                 215                 220

Tyr Thr Tyr Phe His Ala Ala Lys Val Tyr Ile Glu Ala Phe His Thr
225                 230                 235                 240

Val Pro Lys Gly Ile Cys Arg Glu Leu Val Arg Val Met Ala Trp Thr
                245                 250                 255

Phe Phe Val Ala Trp Gly Met Phe Pro Val Leu Phe Leu Leu Gly Thr
            260                 265                 270

Glu Gly Phe Gly His Ile Ser Pro Tyr Gly Ser Ala Ile Gly His Ser
        275                 280                 285

Ile Leu Asp Leu Ile Ala Lys Asn Met Trp Gly Val Leu Gly Asn Tyr
    290                 295                 300

Leu Arg Val Lys Ile His Glu His Ile Leu Leu Tyr Gly Asp Ile Arg
305                 310                 315                 320

Lys Lys Gln Lys Ile Thr Ile Ala Gly Gln Glu Met Glu Val Glu Thr
                325                 330                 335

Leu Val Ala Glu Glu Glu Asp Arg
            340

<210> SEQ ID NO 2
<211> LENGTH: 712
<212> TYPE: PRT
<213> ORGANISM: Chlamydomonas reinhardtii

<400> SEQUENCE: 2

Met Ser Arg Arg Pro Trp Leu Leu Ala Leu Ala Leu Ala Val Ala Leu
1               5                   10                  15

Ala Ala Gly Ser Ala Gly Ala Ser Thr Gly Ser Asp Ala Thr Val Pro
            20                  25                  30

Val Ala Thr Gln Asp Gly Pro Asp Tyr Val Phe His Arg Ala His Glu
        35                  40                  45

Arg Met Leu Phe Gln Thr Ser Tyr Thr Leu Glu Asn Asn Gly Ser Val
    50                  55                  60

Ile Cys Ile Pro Asn Asn Gly Gln Cys Phe Cys Leu Ala Trp Leu Lys
65                  70                  75                  80

Ser Asn Gly Thr Asn Ala Glu Lys Leu Ala Ala Asn Ile Leu Gln Trp
                85                  90                  95

Ile Thr Phe Ala Leu Ser Ala Leu Cys Leu Met Phe Tyr Gly Tyr Gln
            100                 105                 110

Thr Trp Lys Ser Thr Cys Gly Trp Glu Glu Ile Tyr Val Ala Thr Ile
        115                 120                 125

Glu Met Ile Lys Phe Ile Ile Glu Tyr Phe His Glu Phe Asp Glu Pro
    130                 135                 140

Ala Val Ile Tyr Ser Ser Asn Gly Asn Lys Thr Val Trp Leu Arg Tyr
145                 150                 155                 160

Ala Glu Trp Leu Leu Thr Cys Pro Val Ile Leu Ile His Leu Ser Asn
                165                 170                 175

Leu Thr Gly Leu Ala Asn Asp Tyr Asn Lys Arg Thr Met Gly Leu Leu
            180                 185                 190

Val Ser Asp Ile Gly Thr Ile Val Trp Gly Thr Thr Ala Ala Leu Ser
        195                 200                 205

Lys Gly Tyr Val Arg Val Ile Phe Phe Leu Met Gly Leu Cys Tyr Gly
    210                 215                 220

Ile Tyr Thr Phe Phe Asn Ala Ala Lys Val Tyr Ile Glu Ala Tyr His
225                 230                 235                 240

Thr Val Pro Lys Gly Ile Cys Arg Asp Leu Val Arg Tyr Leu Ala Trp
                245                 250                 255

Leu Tyr Phe Cys Ser Trp Ala Met Phe Pro Val Leu Phe Leu Leu Gly
            260                 265                 270

Pro Glu Gly Phe Gly His Ile Asn Gln Phe Asn Ser Ala Ile Ala His
        275                 280                 285

Ala Ile Leu Asp Leu Ala Ser Lys Asn Ala Trp Ser Met Met Gly His
    290                 295                 300

Phe Leu Arg Val Lys Ile His Glu His Ile Leu Leu Tyr Gly Asp Ile
305                 310                 315                 320

Arg Lys Lys Gln Lys Val Asn Val Ala Gly Gln Glu Met Glu Val Glu
                325                 330                 335

Thr Met Val His Glu Glu Asp Asp Glu Thr Gln Lys Val Pro Thr Ala
            340                 345                 350

Lys Tyr Ala Asn Arg Asp Ser Phe Ile Ile Met Arg Asp Arg Leu Lys
        355                 360                 365

Glu Lys Gly Phe Glu Thr Arg Ala Ser Leu Asp Gly Asp Pro Asn Gly
    370                 375                 380

```
Asp Ala Glu Ala Asn Ala Ala Gly Gly Lys Pro Gly Met Glu Met
385                 390                 395                 400

Gly Lys Met Thr Gly Met Gly Met Gly Ala Gly Met Gly Met
                405                 410                 415

Ala Thr Ile Asp Ser Gly Arg Val Ile Leu Ala Val Pro Asp Ile Ser
            420                 425                 430

Met Val Asp Phe Phe Arg Glu Gln Phe Ala Arg Leu Pro Val Pro Tyr
        435                 440                 445

Glu Leu Val Pro Ala Leu Gly Ala Glu Asn Thr Leu Gln Leu Val Gln
    450                 455                 460

Gln Ala Gln Ser Leu Gly Gly Cys Asp Phe Val Leu Met His Pro Glu
465                 470                 475                 480

Phe Leu Arg Asp Arg Ser Pro Thr Gly Leu Leu Pro Arg Leu Lys Met
            485                 490                 495

Gly Gly Gln Arg Ala Ala Ala Phe Gly Trp Ala Ala Ile Gly Pro Met
                500                 505                 510

Arg Asp Leu Ile Glu Gly Ser Gly Val Asp Gly Trp Leu Gly Pro
            515                 520                 525

Ser Phe Gly Ala Gly Ile Asn Gln Gln Ala Leu Val Ala Leu Ile Asn
    530                 535                 540

Arg Met Gln Gln Ala Lys Lys Met Gly Met Met Gly Met Gly Met
545                 550                 555                 560

Gly Met Gly Gly Gly Met Gly Met Gly Met Gly Met Gly Met
                565                 570                 575

Ala Pro Ser Met Asn Ala Gly Met Thr Gly Gly Met Gly Ala Ser
            580                 585                 590

Met Gly Gly Ala Val Met Gly Met Gly Met Gln Pro Met Gln
            595                 600                 605

Gln Ala Met Pro Ala Met Ser Pro Met Met Thr Gln Gln Pro Ser Met
610                 615                 620

Met Ser Gln Pro Ser Ala Met Ser Ala Gly Gly Ala Met Gln Ala Met
625                 630                 635                 640

Gly Gly Val Met Pro Ser Pro Ala Pro Gly Gly Arg Val Gly Thr Asn
                645                 650                 655

Pro Leu Phe Gly Ser Ala Pro Ser Pro Leu Ser Ser Gln Pro Gly Ile
            660                 665                 670

Ser Pro Gly Met Ala Thr Pro Pro Ala Ala Thr Ala Ala Pro Ala Ala
            675                 680                 685

Gly Gly Ser Glu Ala Glu Met Leu Gln Gln Leu Met Ser Glu Ile Asn
    690                 695                 700

Arg Leu Lys Asn Glu Leu Gly Glu
705                 710

<210> SEQ ID NO 3
<211> LENGTH: 316
<212> TYPE: PRT
<213> ORGANISM: Chlamydomonas reinhardtii

<400> SEQUENCE: 3

Met Asp Tyr Gly Gly Ala Leu Ser Ala Val Gly Arg Glu Leu Leu Phe
1               5                   10                  15

Val Thr Asn Pro Val Val Asn Gly Ser Val Leu Val Pro Glu Asp
            20                  25                  30

Gln Cys Tyr Cys Ala Gly Trp Ile Glu Ser Arg Gly Thr Asn Gly Ala
            35                  40                  45
```

Gln Thr Ala Ser Asn Val Leu Gln Trp Leu Ala Ala Gly Phe Ser Ile
            50                  55                  60

Leu Leu Leu Met Phe Tyr Ala Tyr Gln Thr Trp Lys Ser Thr Cys Gly
 65                  70                  75                  80

Trp Glu Glu Ile Tyr Val Cys Ala Ile Glu Met Val Lys Val Ile Leu
                 85                  90                  95

Glu Phe Phe Phe Glu Phe Lys Asn Pro Ser Met Leu Tyr Leu Ala Thr
            100                 105                 110

Gly His Arg Val Gln Trp Leu Arg Tyr Ala Glu Trp Leu Leu Thr Cys
            115                 120                 125

Pro Val Ile Leu Ile His Leu Ser Asn Leu Thr Gly Leu Ser Asn Asp
130                 135                 140

Tyr Ser Arg Arg Thr Met Gly Leu Leu Val Ser Asp Ile Gly Thr Ile
145                 150                 155                 160

Val Trp Gly Ala Thr Ser Ala Met Ala Thr Gly Tyr Val Lys Val Ile
                165                 170                 175

Phe Phe Cys Leu Gly Leu Cys Tyr Gly Ala Asn Thr Phe Phe His Ala
                180                 185                 190

Ala Lys Ala Tyr Ile Glu Gly Tyr His Thr Val Pro Lys Gly Arg Cys
            195                 200                 205

Arg Gln Val Val Thr Gly Met Ala Trp Leu Phe Phe Val Ser Trp Gly
            210                 215                 220

Met Phe Pro Ile Leu Phe Ile Leu Gly Pro Glu Gly Phe Gly Val Leu
225                 230                 235                 240

Ser Val Tyr Gly Ser Thr Val Gly His Thr Ile Ile Asp Leu Met Ser
                245                 250                 255

Lys Asn Cys Trp Gly Leu Leu Gly His Tyr Leu Arg Val Leu Ile His
                260                 265                 270

Glu His Ile Leu Ile His Gly Asp Ile Arg Lys Thr Thr Lys Leu Asn
            275                 280                 285

Ile Gly Gly Thr Glu Ile Glu Val Glu Thr Leu Val Glu Asp Glu Ala
            290                 295                 300

Glu Ala Gly Ala Val Asn Lys Gly Thr Gly Lys Glx
305                 310                 315

<210> SEQ ID NO 4
<211> LENGTH: 342
<212> TYPE: PRT
<213> ORGANISM: Artificial Sequence
<220> FEATURE:
<223> OTHER INFORMATION: Fusion protein, p525

<400> SEQUENCE: 4

Met Ser Arg Arg Pro Trp Leu Leu Ala Leu Ala Leu Ala Val Ala Leu
 1               5                  10                  15

Ala Ala Gly Ser Ala Gly Ala Ser Thr Gly Ser Asp Ala Thr Val Pro
                20                  25                  30

Val Ala Thr Gln Asp Gly Pro Asp Tyr Val Phe His Arg Ala His Glu
             35                  40                  45

Arg Met Leu Phe Gln Thr Ser Tyr Thr Leu Glu Asn Asn Gly Ser Val
         50                  55                  60

Ile Cys Met Pro Arg Gly Gln Cys Tyr Cys Glu Gly Trp Leu Arg Ser
 65                  70                  75                  80

Arg Gly Thr Ser Ile Glu Lys Thr Lys Ile Ala Ile Thr Leu Gln Trp Val
                 85                  90                  95

```
Val Phe Ala Leu Ser Val Ala Cys Leu Gly Trp Tyr Ala Tyr Gln Ala
            100                 105                 110

Trp Arg Ala Thr Cys Gly Trp Glu Glu Val Tyr Val Ala Leu Ile Glu
            115                 120                 125

Met Met Lys Ser Ile Ile Glu Ala Phe His Glu Phe Asp Glu Pro Ala
            130                 135                 140

Val Ile Tyr Ser Ser Asn Gly Asn Lys Thr Val Trp Leu Arg Tyr Ala
145                 150                 155                 160

Glu Trp Leu Leu Thr Cys Pro Val Ile Leu Ile His Leu Ser Asn Leu
                165                 170                 175

Thr Gly Leu Lys Asp Asp Tyr Ser Lys Arg Thr Met Gly Leu Leu Val
            180                 185                 190

Ser Asp Val Gly Cys Ile Val Trp Gly Ala Thr Ser Ala Met Cys Thr
            195                 200                 205

Gly Trp Thr Lys Ile Leu Phe Phe Leu Ile Ser Leu Ser Tyr Gly Met
            210                 215                 220

Tyr Thr Tyr Phe His Ala Ala Lys Val Tyr Ile Glu Ala Phe His Thr
225                 230                 235                 240

Val Pro Lys Gly Ile Cys Arg Glu Leu Val Arg Val Met Ala Trp Thr
                245                 250                 255

Phe Phe Val Ala Trp Gly Met Phe Pro Val Leu Phe Leu Leu Gly Pro
            260                 265                 270

Glu Gly Phe Gly Val Leu Ser Val Tyr Gly Ser Ala Ile Gly His Ser
            275                 280                 285

Ile Leu Asp Leu Ile Ala Lys Asn Met Trp Gly Val Leu Gly Asn Tyr
            290                 295                 300

Leu Arg Val Lys Ile His Glu His Ile Leu Leu Tyr Gly Asp Ile Arg
305                 310                 315                 320

Lys Lys Gln Lys Ile Thr Ile Ala Gly Gln Glu Met Glu Val Glu Thr
                325                 330                 335

Leu Val Ala Glu Glu Glu
            340

<210> SEQ ID NO 5
<211> LENGTH: 289
<212> TYPE: PRT
<213> ORGANISM: Chloromonas oogama

<400> SEQUENCE: 5

Met Leu Gly Asn Gly Ser Ala Ile Val Pro Ile Asp Gln Cys Phe Cys
1               5                   10                  15

Leu Ala Trp Thr Asp Ser Leu Gly Ser Asp Thr Glu Gln Leu Val Ala
            20                  25                  30

Asn Ile Leu Gln Trp Phe Ala Phe Gly Phe Ser Ile Leu Ile Leu Met
            35                  40                  45

Phe Tyr Ala Tyr Gln Thr Trp Arg Ala Thr Cys Gly Trp Glu Glu Val
            50                  55                  60

Tyr Val Cys Cys Val Glu Leu Thr Lys Val Ile Ile Glu Phe Phe His
65                  70                  75                  80

Glu Phe Asp Asp Pro Ser Met Leu Tyr Leu Ala Asn Gly His Arg Val
                85                  90                  95

Gln Trp Leu Arg Tyr Ala Glu Trp Leu Leu Thr Cys Pro Val Ile Leu
            100                 105                 110

Ile His Leu Ser Asn Leu Thr Gly Leu Lys Asp Asp Tyr Ser Lys Arg
```

```
                115                 120                 125
Thr Met Arg Leu Leu Val Ser Asp Val Gly Thr Ile Val Trp Gly Ala
        130                 135                 140
Thr Ser Ala Met Ser Thr Gly Tyr Val Lys Val Ile Phe Phe Val Leu
145                 150                 155                 160
Gly Cys Ile Tyr Gly Ala Asn Thr Phe Phe His Ala Ala Lys Val Tyr
                165                 170                 175
Ile Glu Ser Tyr His Val Val Pro Lys Gly Arg Pro Arg Thr Val Val
                180                 185                 190
Arg Ile Met Ala Trp Leu Phe Phe Leu Ser Trp Gly Met Phe Pro Val
                195                 200                 205
Leu Phe Val Val Gly Pro Glu Gly Phe Asp Ala Ile Ser Val Tyr Gly
        210                 215                 220
Ser Thr Ile Gly His Thr Ile Ile Asp Leu Met Ser Lys Asn Cys Trp
225                 230                 235                 240
Gly Leu Leu Gly His Tyr Leu Arg Val Leu Ile His Gln His Ile Ile
                245                 250                 255
Ile Tyr Gly Asp Ile Arg Lys Lys Thr Lys Ile Asn Val Ala Gly Glu
                260                 265                 270
Glu Met Glu Val Glu Thr Met Val Asp Gln Asp Glu Glu Thr Val
        275                 280                 285
Glx

<210> SEQ ID NO 6
<211> LENGTH: 344
<212> TYPE: PRT
<213> ORGANISM: Artificial Sequence
<220> FEATURE:
<223> OTHER INFORMATION: Fusion protein, p548

<400> SEQUENCE: 6

Met Ser Arg Arg Pro Trp Leu Leu Ala Leu Ala Leu Ala Val Ala Leu
1               5                   10                  15
Ala Ala Gly Ser Ala Gly Ala Ser Thr Gly Ser Asp Ala Thr Val Pro
                20                  25                  30
Val Ala Thr Gln Asp Gly Pro Asp Tyr Val Phe His Arg Ala His Glu
        35                  40                  45
Arg Met Leu Phe Gln Thr Ser Tyr Thr Leu Glu Asn Asn Gly Ser Val
    50                  55                  60
Ile Cys Met Pro Arg Gly Gln Cys Tyr Cys Glu Gly Trp Leu Arg Ser
65                  70                  75                  80
Arg Gly Thr Ser Ile Glu Lys Thr Ile Ala Ile Thr Leu Gln Trp Val
                85                  90                  95
Val Phe Ala Leu Ser Val Ala Cys Leu Gly Trp Tyr Ala Tyr Gln Ala
                100                 105                 110
Trp Arg Ala Thr Cys Gly Trp Glu Glu Val Tyr Val Ala Leu Ile Glu
                115                 120                 125
Met Met Lys Ser Ile Ile Glu Ala Phe His Glu Phe Asp Glu Pro Ala
        130                 135                 140
Val Ile Tyr Ser Ser Asn Gly Asn Lys Thr Val Trp Leu Arg Tyr Ala
145                 150                 155                 160
Glu Trp Leu Leu Thr Cys Pro Val Ile Leu Ile His Leu Ser Asn Leu
                165                 170                 175
Thr Gly Leu Lys Asp Asp Tyr Ser Lys Arg Thr Met Gly Leu Leu Val
                180                 185                 190
```

Ser Asp Val Gly Cys Ile Val Trp Gly Ala Thr Ser Ala Met Cys Thr
        195                 200                 205

Gly Trp Thr Lys Ile Leu Phe Phe Leu Ile Ser Leu Ser Tyr Gly Met
210                 215                 220

Tyr Thr Tyr Phe His Ala Ala Lys Val Tyr Ile Glu Ala Phe His Thr
225                 230                 235                 240

Val Pro Lys Gly Arg Pro Arg Thr Val Arg Ile Met Ala Trp Leu
                245                 250                 255

Phe Phe Leu Ser Trp Gly Met Phe Pro Val Leu Phe Val Val Gly Pro
                260                 265                 270

Glu Gly Phe Gly Val Leu Ser Val Tyr Gly Ser Ala Ile Gly His Ser
                275                 280                 285

Ile Leu Asp Leu Ile Ala Lys Asn Met Trp Gly Val Leu Gly Asn Tyr
        290                 295                 300

Leu Arg Val Lys Ile His Glu His Ile Leu Leu Tyr Gly Asp Ile Arg
305                 310                 315                 320

Lys Lys Thr Lys Ile Asn Val Ala Gly Glu Glu Met Glu Val Glu Thr
                325                 330                 335

Met Val Asp Gln Glu Asp Glu Glu
            340

<210> SEQ ID NO 7
<211> LENGTH: 311
<212> TYPE: PRT
<213> ORGANISM: Artificial Sequence
<220> FEATURE:
<223> OTHER INFORMATION: Fusion protein, p550

<400> SEQUENCE: 7

Met Ser Arg Arg Pro Trp Leu Leu Ala Leu Ala Leu Ala Val Ala Leu
1               5                   10                  15

Ala Ala Gly Ser Ala Gly Ala Ser Thr Gly Ser Asn Gly Ser Val Ile
                20                  25                  30

Cys Met Pro Arg Gly Gln Cys Tyr Cys Glu Gly Trp Leu Arg Ser Arg
            35                  40                  45

Gly Thr Ser Ile Glu Lys Thr Ile Ala Ile Thr Leu Gln Trp Val Val
    50                  55                  60

Phe Ala Leu Ser Val Ala Cys Leu Gly Trp Tyr Ala Tyr Gln Ala Trp
65                  70                  75                  80

Arg Ala Thr Cys Gly Trp Glu Glu Val Tyr Val Ala Leu Ile Glu Met
                85                  90                  95

Met Lys Ser Ile Ile Glu Ala Phe His Glu Phe Asp Glu Pro Ala Val
            100                 105                 110

Ile Tyr Ser Ser Asn Gly Asn Lys Thr Val Trp Leu Arg Tyr Ala Glu
        115                 120                 125

Trp Leu Leu Thr Cys Pro Val Ile Leu Ile His Leu Ser Asn Leu Thr
    130                 135                 140

Gly Leu Lys Asp Asp Tyr Ser Lys Arg Thr Met Gly Leu Leu Val Ser
145                 150                 155                 160

Asp Val Gly Cys Ile Val Trp Gly Ala Thr Ser Ala Met Cys Thr Gly
                165                 170                 175

Trp Thr Lys Ile Leu Phe Phe Leu Ile Ser Leu Ser Tyr Gly Met Tyr
            180                 185                 190

Thr Tyr Phe His Ala Ala Lys Val Tyr Ile Glu Ala Phe His Thr Val
        195                 200                 205

```
Pro Lys Gly Arg Pro Arg Thr Val Val Arg Ile Met Ala Trp Leu Phe
    210                 215                 220

Phe Leu Ser Trp Gly Met Phe Pro Val Leu Phe Val Val Gly Pro Glu
225                 230                 235                 240

Gly Phe Gly Val Leu Ser Val Tyr Gly Ser Ala Ile Gly His Ser Ile
                245                 250                 255

Leu Asp Leu Ile Ala Lys Asn Met Trp Gly Val Leu Gly Asn Tyr Leu
                260                 265                 270

Arg Val Lys Ile His Glu His Ile Leu Leu Tyr Gly Asp Ile Arg Lys
            275                 280                 285

Lys Thr Lys Ile Asn Val Ala Gly Glu Glu Met Glu Val Glu Thr Met
    290                 295                 300

Val Asp Gln Glu Asp Glu Glu
305                 310

<210> SEQ ID NO 8
<211> LENGTH: 344
<212> TYPE: PRT
<213> ORGANISM: Artificial Sequence
<220> FEATURE:
<223> OTHER INFORMATION: Fusion protein, p528

<400> SEQUENCE: 8

Met Ser Arg Arg Pro Trp Leu Leu Ala Leu Ala Leu Ala Val Ala Leu
1               5                   10                  15

Ala Ala Gly Ser Ala Gly Ala Ser Thr Gly Ser Asp Ala Thr Val Pro
                20                  25                  30

Val Ala Thr Gln Asp Gly Pro Asp Tyr Val Phe His Arg Ala His Glu
            35                  40                  45

Arg Met Leu Phe Gln Thr Ser Tyr Thr Leu Glu Asn Asn Gly Ser Val
        50                  55                  60

Ile Cys Met Pro Arg Gly Gln Cys Tyr Cys Glu Gly Trp Leu Arg Ser
65                  70                  75                  80

Arg Gly Thr Ser Ile Glu Lys Thr Ile Ala Ile Thr Leu Gln Trp Val
                85                  90                  95

Val Phe Ala Leu Ser Val Ala Cys Leu Gly Trp Tyr Ala Tyr Gln Ala
            100                 105                 110

Trp Arg Ala Thr Cys Gly Trp Glu Glu Val Tyr Val Ala Leu Ile Glu
        115                 120                 125

Met Met Lys Ser Ile Ile Glu Ala Phe His Glu Phe Asp Glu Pro Ala
130                 135                 140

Val Ile Tyr Ser Ser Asn Gly Asn Lys Thr Val Trp Leu Arg Tyr Ala
145                 150                 155                 160

Glu Trp Leu Leu Thr Cys Pro Val Ile Leu Ile His Leu Ser Asn Leu
                165                 170                 175

Thr Gly Leu Lys Asp Asp Tyr Ser Lys Arg Thr Met Gly Leu Leu Val
            180                 185                 190

Ser Asp Val Gly Cys Ile Val Trp Gly Ala Thr Ser Ala Met Cys Thr
        195                 200                 205

Gly Tyr Val Lys Ile Leu Phe Phe Leu Ile Ser Leu Ser Tyr Gly Met
210                 215                 220

Tyr Thr Tyr Phe His Ala Ala Lys Val Tyr Ile Glu Ala Phe His Thr
225                 230                 235                 240

Val Pro Lys Gly Ile Cys Arg Glu Leu Val Arg Val Met Ala Trp Thr
                245                 250                 255
```

```
Phe Phe Val Ala Trp Gly Met Phe Pro Val Leu Phe Leu Leu Gly Pro
            260                 265                 270

Glu Gly Phe Gly Val Leu Ser Val Tyr Gly Ser Ala Ile Gly His Ser
        275                 280                 285

Ile Leu Asp Leu Ile Ala Lys Asn Met Trp Gly Val Leu Gly Asn Tyr
    290                 295                 300

Leu Arg Val Lys Ile His Glu His Ile Leu Leu Tyr Gly Asp Ile Arg
305                 310                 315                 320

Lys Lys Gln Lys Ile Thr Ile Ala Gly Gln Glu Met Glu Val Glu Thr
                325                 330                 335

Leu Val Ala Glu Glu Asp Arg
            340

<210> SEQ ID NO 9
<211> LENGTH: 344
<212> TYPE: PRT
<213> ORGANISM: Artificial Sequence
<220> FEATURE:
<223> OTHER INFORMATION: Fusion protein, p578

<400> SEQUENCE: 9

Met Ser Arg Arg Pro Trp Leu Leu Ala Leu Ala Leu Ala Val Ala Leu
1               5                   10                  15

Ala Ala Gly Ser Ala Gly Ala Ser Thr Gly Ser Asp Ala Thr Val Pro
            20                  25                  30

Val Ala Thr Gln Asp Gly Pro Asp Tyr Val Phe His Arg Ala His Glu
        35                  40                  45

Arg Met Leu Phe Gln Thr Ser Tyr Thr Leu Glu Asn Asn Gly Ser Val
    50                  55                  60

Ile Cys Met Pro Arg Gly Gln Cys Tyr Cys Glu Gly Trp Leu Arg Ser
65                  70                  75                  80

Arg Gly Thr Ser Ile Glu Lys Thr Ile Ala Ile Thr Leu Gln Trp Val
                85                  90                  95

Val Phe Ala Leu Ser Val Ala Cys Leu Gly Trp Tyr Ala Tyr Gln Ala
            100                 105                 110

Trp Arg Ala Thr Cys Gly Trp Glu Glu Val Tyr Val Ala Leu Ile Glu
        115                 120                 125

Met Met Lys Ser Ile Ile Glu Ala Phe His Glu Phe Asp Glu Pro Ala
    130                 135                 140

Val Ile Tyr Ser Ser Asn Gly Asn Lys Thr Val Trp Leu Arg Tyr Ala
145                 150                 155                 160

Glu Trp Leu Leu Thr Cys Pro Val Ile Leu Ile Gly Leu Ser Asn Leu
                165                 170                 175

Thr Gly Leu Lys Asp Asp Tyr Ser Lys Arg Thr Met Gly Leu Leu Val
            180                 185                 190

Ser Asp Val Gly Cys Ile Val Trp Gly Ala Thr Ser Ala Met Cys Thr
        195                 200                 205

Gly Trp Thr Lys Ile Leu Phe Phe Leu Ile Ser Leu Ser Tyr Gly Met
    210                 215                 220

Tyr Thr Tyr Phe His Ala Ala Lys Val Tyr Ile Glu Ala Phe His Thr
225                 230                 235                 240

Val Pro Lys Gly Arg Pro Arg Thr Val Val Arg Ile Met Ala Trp Leu
                245                 250                 255

Phe Phe Leu Ser Trp Gly Met Phe Pro Val Leu Phe Val Val Gly Pro
            260                 265                 270
```

```
Glu Gly Phe Gly Val Leu Ser Val Tyr Gly Ser Ala Ile Gly His Ser
            275                 280                 285

Ile Leu Asp Leu Ile Ala Lys Asn Met Trp Gly Val Leu Gly Asn Tyr
    290                 295                 300

Leu Arg Val Lys Ile His Glu His Ile Leu Leu Tyr Gly Asp Ile Arg
305                 310                 315                 320

Lys Lys Thr Lys Ile Asn Val Ala Gly Glu Glu Met Glu Val Glu Thr
                325                 330                 335

Met Val Asp Gln Glu Asp Glu Glu
            340

<210> SEQ ID NO 10
<211> LENGTH: 344
<212> TYPE: PRT
<213> ORGANISM: Artificial Sequence
<220> FEATURE:
<223> OTHER INFORMATION: Fusion protein, p579

<400> SEQUENCE: 10

Met Ser Arg Arg Pro Trp Leu Leu Ala Leu Ala Leu Ala Val Ala Leu
1               5                   10                  15

Ala Ala Gly Ser Ala Gly Ala Ser Thr Gly Ser Asp Ala Thr Val Pro
            20                  25                  30

Val Ala Thr Gln Asp Gly Pro Asp Tyr Val Phe His Arg Ala His Glu
        35                  40                  45

Arg Met Leu Phe Gln Thr Ser Tyr Thr Leu Glu Asn Asn Gly Ser Val
    50                  55                  60

Ile Cys Met Pro Arg Gly Gln Cys Tyr Cys Glu Gly Trp Leu Arg Ser
65                  70                  75                  80

Arg Gly Thr Ser Ile Glu Lys Thr Ile Ala Ile Thr Leu Gln Trp Val
                85                  90                  95

Val Phe Ala Leu Ser Val Ala Cys Leu Gly Trp Tyr Ala Tyr Gln Ala
            100                 105                 110

Trp Arg Ala Thr Cys Gly Trp Glu Glu Val Tyr Val Ala Leu Ile Glu
        115                 120                 125

Met Met Lys Ser Ile Ile Glu Ala Phe His Glu Phe Asp Glu Pro Ala
    130                 135                 140

Val Ile Tyr Ser Ser Asn Gly Asn Lys Thr Val Trp Leu Arg Tyr Ala
145                 150                 155                 160

Glu Trp Leu Leu Thr Cys Pro Val Ile Leu Ile Ala Leu Ser Asn Leu
                165                 170                 175

Thr Gly Leu Lys Asp Asp Tyr Ser Lys Arg Thr Met Gly Leu Leu Val
            180                 185                 190

Ser Asp Val Gly Cys Ile Val Trp Gly Ala Thr Ser Ala Met Cys Thr
        195                 200                 205

Gly Trp Thr Lys Ile Leu Phe Phe Leu Ile Ser Leu Ser Tyr Gly Met
    210                 215                 220

Tyr Thr Tyr Phe His Ala Ala Lys Val Tyr Ile Glu Ala Phe His Thr
225                 230                 235                 240

Val Pro Lys Gly Arg Pro Arg Thr Val Val Arg Ile Met Ala Trp Leu
                245                 250                 255

Phe Phe Leu Ser Trp Gly Met Phe Pro Val Leu Phe Val Val Gly Pro
            260                 265                 270

Glu Gly Phe Gly Val Leu Ser Val Tyr Gly Ser Ala Ile Gly His Ser
        275                 280                 285
```

```
Ile Leu Asp Leu Ile Ala Lys Asn Met Trp Gly Val Leu Gly Asn Tyr
    290                 295                 300

Leu Arg Val Lys Ile His Glu His Ile Leu Leu Tyr Gly Asp Ile Arg
305                 310                 315                 320

Lys Lys Thr Lys Ile Asn Val Ala Gly Glu Glu Met Glu Val Glu Thr
                325                 330                 335

Met Val Asp Gln Glu Asp Glu Glu
            340

<210> SEQ ID NO 11
<211> LENGTH: 344
<212> TYPE: PRT
<213> ORGANISM: Artificial Sequence
<220> FEATURE:
<223> OTHER INFORMATION: Fusion protein, p580

<400> SEQUENCE: 11

Met Ser Arg Arg Pro Trp Leu Leu Ala Leu Ala Leu Ala Val Ala Leu
1               5                   10                  15

Ala Ala Gly Ser Ala Gly Ala Ser Thr Gly Ser Asp Ala Thr Val Pro
            20                  25                  30

Val Ala Thr Gln Asp Gly Pro Asp Tyr Val Phe His Arg Ala His Glu
        35                  40                  45

Arg Met Leu Phe Gln Thr Ser Tyr Thr Leu Glu Asn Asn Gly Ser Val
    50                  55                  60

Ile Cys Met Pro Arg Gly Gln Cys Tyr Cys Glu Gly Trp Leu Arg Ser
65                  70                  75                  80

Arg Gly Thr Ser Ile Glu Lys Thr Ile Ala Ile Thr Leu Gln Trp Val
                85                  90                  95

Val Phe Ala Leu Ser Val Ala Cys Leu Gly Trp Tyr Ala Tyr Gln Ala
            100                 105                 110

Trp Arg Ala Thr Cys Gly Trp Glu Glu Val Tyr Val Ala Leu Ile Glu
        115                 120                 125

Met Met Lys Ser Ile Ile Glu Ala Phe His Glu Phe Asp Glu Pro Ala
    130                 135                 140

Val Ile Tyr Ser Ser Asn Gly Asn Lys Thr Val Trp Leu Arg Tyr Ala
145                 150                 155                 160

Glu Trp Leu Leu Thr Cys Pro Val Ile Leu Ile Lys Leu Ser Asn Leu
                165                 170                 175

Thr Gly Leu Lys Asp Asp Tyr Ser Lys Arg Thr Met Gly Leu Leu Val
            180                 185                 190

Ser Asp Val Gly Cys Ile Val Trp Gly Ala Thr Ser Ala Met Cys Thr
        195                 200                 205

Gly Trp Thr Lys Ile Leu Phe Phe Leu Ile Ser Leu Ser Tyr Gly Met
    210                 215                 220

Tyr Thr Tyr Phe His Ala Ala Lys Val Tyr Ile Glu Ala Phe His Thr
225                 230                 235                 240

Val Pro Lys Gly Arg Pro Arg Thr Val Val Arg Ile Met Ala Trp Leu
                245                 250                 255

Phe Phe Leu Ser Trp Gly Met Phe Pro Val Leu Phe Val Gly Pro
            260                 265                 270

Glu Gly Phe Gly Val Leu Ser Val Tyr Gly Ser Ala Ile Gly His Ser
        275                 280                 285

Ile Leu Asp Leu Ile Ala Lys Asn Met Trp Gly Val Leu Gly Asn Tyr
    290                 295                 300
```

```
Leu Arg Val Lys Ile His Glu His Ile Leu Leu Tyr Gly Asp Ile Arg
305                 310                 315                 320

Lys Lys Thr Lys Ile Asn Val Ala Gly Glu Glu Met Glu Val Glu Thr
                325                 330                 335

Met Val Asp Gln Glu Asp Glu Glu
            340
```

```
<210> SEQ ID NO 12
<211> LENGTH: 344
<212> TYPE: PRT
<213> ORGANISM: Artificial Sequence
<220> FEATURE:
<223> OTHER INFORMATION: Fusion protein, p581

<400> SEQUENCE: 12
```

```
Met Ser Arg Arg Pro Trp Leu Leu Ala Leu Ala Leu Ala Val Ala Leu
1                 5                   10                  15

Ala Ala Gly Ser Ala Gly Ala Ser Thr Gly Ser Asp Ala Thr Val Pro
                20                  25                  30

Val Ala Thr Gln Asp Gly Pro Asp Tyr Val Phe His Arg Ala His Glu
            35                  40                  45

Arg Met Leu Phe Gln Thr Ser Tyr Thr Leu Glu Asn Asn Gly Ser Val
        50                  55                  60

Ile Cys Met Pro Arg Gly Gln Cys Tyr Cys Glu Gly Trp Leu Arg Ser
65                  70                  75                  80

Arg Gly Thr Ser Ile Glu Lys Thr Ile Ala Ile Thr Leu Gln Trp Val
                85                  90                  95

Val Phe Ala Leu Ser Val Ala Cys Leu Gly Trp Tyr Ala Tyr Gln Ala
            100                 105                 110

Trp Arg Ala Thr Cys Gly Trp Glu Glu Val Tyr Val Ala Leu Ile Glu
        115                 120                 125

Met Met Lys Ser Ile Ile Glu Ala Phe His Glu Phe Asp Glu Pro Ala
130                 135                 140

Val Ile Tyr Ser Ser Asn Gly Asn Lys Thr Val Trp Leu Arg Tyr Ala
145                 150                 155                 160

Glu Trp Leu Leu Thr Cys Pro Val Ile Leu Ile Arg Leu Ser Asn Leu
                165                 170                 175

Thr Gly Leu Lys Asp Asp Tyr Ser Lys Arg Thr Met Gly Leu Leu Val
            180                 185                 190

Ser Asp Val Gly Cys Ile Val Trp Gly Ala Thr Ser Ala Met Cys Thr
        195                 200                 205

Gly Trp Thr Lys Ile Leu Phe Phe Leu Ile Ser Leu Ser Tyr Gly Met
210                 215                 220

Tyr Thr Tyr Phe His Ala Ala Lys Val Tyr Ile Glu Ala Phe His Thr
225                 230                 235                 240

Val Pro Lys Gly Arg Pro Arg Thr Val Val Arg Ile Met Ala Trp Leu
                245                 250                 255

Phe Phe Leu Ser Trp Gly Met Phe Pro Val Leu Phe Val Val Gly Pro
            260                 265                 270

Glu Gly Phe Gly Val Leu Ser Val Tyr Gly Ser Ala Ile Gly His Ser
        275                 280                 285

Ile Leu Asp Leu Ile Ala Lys Asn Met Trp Gly Val Leu Gly Asn Tyr
290                 295                 300

Leu Arg Val Lys Ile His Glu His Ile Leu Leu Tyr Gly Asp Ile Arg
305                 310                 315                 320
```

Lys Lys Thr Lys Ile Asn Val Ala Gly Glu Glu Met Glu Val Glu Thr
            325                 330                 335

Met Val Asp Gln Glu Asp Glu Glu
            340

<210> SEQ ID NO 13
<211> LENGTH: 1026
<212> TYPE: DNA
<213> ORGANISM: Artificial Sequence
<220> FEATURE:
<223> OTHER INFORMATION: DNA encoding fusion protein, p525

<400> SEQUENCE: 13

| | | |
|---|---|---|
| atgtctagaa ggccttggct gcttgctctg gctctggctg ttgcacttgc tgctggatct | 60 |
| gctggcgcct ctacaggatc tgatgctaca gtgccagtgg ccacacagga cggccctgat | 120 |
| tatgtgtttc acagagccca cgagcggatg ctgttccaga ccagctacac cctggaaaac | 180 |
| aacggcagcg tgatctgcat gcccagaggc cagtgttact gcgaaggctg gctgagaagc | 240 |
| agaggcacca gcatcgagaa acaatcgcc atcactctgc agtgggtcgt gtttgccctg | 300 |
| tctgtggcct gtctcggatg gtacgcttac caggcttgga gagccacctg tggctgggaa | 360 |
| gaagtgtacg tcgccctgat cgagatgatg aagtccatca tcgaggcctt ccacgagttc | 420 |
| gacgagcctg ccgtgatcta cagctccaac ggcaacaaga ccgtgtggct gagatatgcc | 480 |
| gagtggctgc tgacctgtcc tgtgatcctg atccacctga gcaacctgac cggcctgaag | 540 |
| gacgactaca gcaagagaac aatgggcctg ctggtgtccg atgtgggctg tattgtgtgg | 600 |
| ggagccacct ctgccatgtg taccggatgg accaagatcc tgttcttcct gatcagcctg | 660 |
| tcctacggca tgtacaccta cttccacgcc gccaaagtgt acattgaggc ctttcacaca | 720 |
| gtgcccaagg gcatctgcag agaactcgtc agagtcatgg cctggacctt tttcgtggcc | 780 |
| tggggaatgt tccccgtgct gtttctgctg ggccctgaag gctttggcgt gctgtctgtg | 840 |
| tatggctctg ccatcggcca cagcatcctg gacctgatcg ccaagaatat gtggggcgtg | 900 |
| ctgggcaact acctgagagt gaagatccac gagcacatcc tgctgtacgg cgacatccgg | 960 |
| aagaagcaga gatcacaat cgccggccaa gagatggaag tggaaccct ggtggccgag | 1020 |
| gaagag | 1026 |

<210> SEQ ID NO 14
<211> LENGTH: 1032
<212> TYPE: DNA
<213> ORGANISM: Artificial Sequence
<220> FEATURE:
<223> OTHER INFORMATION: DNA encoding fusion protein, p548

<400> SEQUENCE: 14

| | | |
|---|---|---|
| atgtctagaa ggccttggct gcttgctctg gctctggctg ttgcacttgc tgctggatct | 60 |
| gctggcgcct ctacaggatc tgatgctaca gtgccagtgg ccacacagga cggccctgat | 120 |
| tatgtgtttc acagagccca cgagcggatg ctgttccaga ccagctacac cctggaaaac | 180 |
| aacggcagcg tgatctgcat gcccagaggc cagtgttact gcgaaggctg gctgagaagc | 240 |
| agaggcacca gcatcgagaa acaatcgcc atcactctgc agtgggtcgt gtttgccctg | 300 |
| tctgtggcct gtctcggatg gtacgcttac caggcttgga gagccacctg tggctgggaa | 360 |
| gaagtgtacg tcgccctgat cgagatgatg aagtccatca tcgaggcctt ccacgagttc | 420 |
| gacgagcctg ccgtgatcta cagctccaac ggcaacaaga ccgtgtggct gagatatgcc | 480 |

| | |
|---|---|
| gagtggctgc tgacctgtcc tgtgatcctg atccacctga gcaacctgac cggcctgaag | 540 |
| gacgactaca gcaagagaac aatgggcctg ctggtgtccg atgtgggctg tattgtgtgg | 600 |
| ggagccacct ctgccatgtg taccggatgg accaagatcc tgttcttcct gatcagcctg | 660 |
| tcctacggca tgtacaccta cttccacgcc gccaaagtgt acattgaggc ctttcacaca | 720 |
| gtgcccaagg gcagacctag aaccgtggtg agaatcatgg cttggctgtt ctttctgagc | 780 |
| tggggcatgt tccccgtgct gttcgtcgtg ggccctgaag gctttggcgt gctgtctgtg | 840 |
| tatggctctg ccatcggcca cagcatcctg gacctgatcg ccaagaatat gtggggcgtg | 900 |
| ctgggcaact acctgagagt gaagatccac gagcacatcc tgctgtacgg cgacatccgg | 960 |
| aagaagacca agatcaacgt ggccggcgag gagatggaag tggagaccat ggtggaccag | 1020 |
| gaggacgagg ag | 1032 |

<210> SEQ ID NO 15
<211> LENGTH: 933
<212> TYPE: DNA
<213> ORGANISM: Artificial Sequence
<220> FEATURE:
<223> OTHER INFORMATION: DNA encoding fusion protein, p550

<400> SEQUENCE: 15

| | |
|---|---|
| atgtctagaa ggccttggct gcttgctctg ctctggctg ttgcacttgc tgctggatct | 60 |
| gctggcgcct ctacaggatc taacggcagc gtgatctgca tgcccagagg ccagtgttac | 120 |
| tgcgaaggct ggctgagaag cagaggcacc agcatcgaga aacaatcgc catcactctg | 180 |
| cagtgggtcg tgtttgccct gtctgtggcc tgtctcggat ggtacgctta ccaggcttgg | 240 |
| agagccacct gtggctggga agaagtgtac gtcgccctga tcgagatgat gaagtccatc | 300 |
| atcgaggcct tccacgagtt cgacgagcct gccgtgatct acagctccaa cggcaacaag | 360 |
| accgtgtggc tgagatatgc cgagtggctg ctgacctgtc ctgtgatcct gatccacctg | 420 |
| agcaacctga ccggcctgaa ggacgactac agcaagagaa caatgggcct gctggtgtcc | 480 |
| gatgtgggct gtattgtgtg gggagccacc tctgccatgt gtaccggatg gaccaagatc | 540 |
| ctgttcttcc tgatcagcct gtcctacggc atgtacacct acttccacgc cgccaaagtg | 600 |
| tacattgagg cctttcacac agtgcccaag ggcagaccta gaaccgtggt gagaatcatg | 660 |
| gcttggctgt tctttctgag ctggggcatg ttccccgtgc tgttcgtggt gggccctgaa | 720 |
| ggctttggcg tgctgtctgt gtatggctct gccatcggcc acagcatcct ggacctgatc | 780 |
| gccaagaata tgtggggcgt gctgggcaac tacctgagag tgaagatcca cgagcacatc | 840 |
| ctgctgtacg gcgacatccg gaagaagacc aagatcaacg tggccggcga ggagatggaa | 900 |
| gtggagacca tggtggacca ggaggacgag gag | 933 |

<210> SEQ ID NO 16
<211> LENGTH: 1032
<212> TYPE: DNA
<213> ORGANISM: Artificial Sequence
<220> FEATURE:
<223> OTHER INFORMATION: DNA encoding fusion protein, p528

<400> SEQUENCE: 16

| | |
|---|---|
| atgtctagaa ggccttggct gcttgctctg ctctggctg ttgcacttgc tgctggatct | 60 |
| gctggcgcct ctacaggatc tgatgctaca gtgccagtgg ccacacagga cggccctgat | 120 |
| tatgtgtttc acagagccca cgagcggatg ctgttccaga ccagctacac cctggaaaac | 180 |
| aacggcagcg tgatctgcat gcccagaggc cagtgttact gcgaaggctg gctgagaagc | 240 |

| | |
|---|---|
| agaggcacca gcatcgagaa aacaatcgcc atcactctgc agtgggtcgt gtttgccctg | 300 |
| tctgtggcct gtctcggatg gtacgcttac caggcttgga gagccacctg tggctgggaa | 360 |
| gaagtgtacg tcgccctgat cgagatgatg aagtccatca tcgaggcctt ccacgagttc | 420 |
| gacgagcctg ccgtgatcta cagctccaac ggcaacaaga ccgtgtggct gagatatgcc | 480 |
| gagtggctgc tgacctgtcc tgtgatcctg atccacctga gcaacctgac cggcctgaag | 540 |
| gacgactaca gcaagagaac aatgggcctg ctggtgtccg atgtgggctg tattgtgtgg | 600 |
| ggagccacca gcgccatgtg taccggctat gtgaagatcc tgttcttcct gatcagcctg | 660 |
| tcctacggca tgtacaccta cttccacgcc gccaaagtgt acatcgaggc cttccacaca | 720 |
| gtgcccaagg gcatctgcag agaactcgtc agagtcatgg cctggacctt tttcgtggcc | 780 |
| tggggaatgt tccccgtgct gtttctgctg ggccctgaag gctttggcgt gctgtctgtg | 840 |
| tatggctctg ccatcggcca cagcatcctg gacctgatcg ccaagaatat gtggggcgtg | 900 |
| ctgggcaact acctgagagt gaagatccac gagcacatcc tgctgtacgg cgacatccgg | 960 |
| aagaagcaga agatcacaat cgccggccaa gagatggaag tggaaaccct ggtggccgag | 1020 |
| gaagaggatc gg | 1032 |

<210> SEQ ID NO 17
<211> LENGTH: 1032
<212> TYPE: DNA
<213> ORGANISM: Artificial Sequence
<220> FEATURE:
<223> OTHER INFORMATION: DNA encoding fusion protein, p578

<400> SEQUENCE: 17

| | |
|---|---|
| atgtctagaa ggccttggct gcttgctctg gctctggctg ttgcacttgc tgctggatct | 60 |
| gctggcgcct ctacaggatc tgatgctaca gtgccagtgg ccacacagga cggccctgat | 120 |
| tatgtgtttc acagagccca cgagcggatg ctgttccaga ccagctacac cctggaaaac | 180 |
| aacggcagcg tgatctgcat gcccagaggc cagtgttact gcgaaggctg gctgagaagc | 240 |
| agaggcacca gcatcgagaa aacaatcgcc atcactctgc agtgggtcgt gtttgccctg | 300 |
| tctgtggcct gtctcggatg gtacgcttac caggcttgga gagccacctg tggctgggaa | 360 |
| gaagtgtacg tcgccctgat cgagatgatg aagtccatca tcgaggcctt ccacgagttc | 420 |
| gacgagcctg ccgtgatcta cagctccaac ggcaacaaga ccgtgtggct gagatatgcc | 480 |
| gagtggctgc tgacctgtcc tgtgatcctg atcggactga gcaacctgac cggcctgaag | 540 |
| gacgactaca gcaagagaac aatgggcctg ctggtgtccg atgtgggctg tattgtgtgg | 600 |
| ggagccacct ctgccatgtg taccggatgg accaagatcc tgttcttcct gatcagcctg | 660 |
| tcctacggca tgtacaccta cttccacgcc gccaaagtgt acattgaggc ctttcacaca | 720 |
| gtgcccaagg gcagacctag aaccgtggtg agaatcatgg cttggctgtt ctttctgagc | 780 |
| tggggcatgt tccccgtgct gttcgtggtg ggccctgaag gctttggcgt gctgtctgtg | 840 |
| tatggctctg ccatcggcca cagcatcctg gacctgatcg ccaagaatat gtggggcgtg | 900 |
| ctgggcaact acctgagagt gaagatccac gagcacatcc tgctgtacgg cgacatccgg | 960 |
| aagaagacca gatcaacgt ggccggcgag gagatggaag tggagaccat ggtggaccag | 1020 |
| gaggacgagg ag | 1032 |

<210> SEQ ID NO 18
<211> LENGTH: 1032
<212> TYPE: DNA

<213> ORGANISM: Artificial Sequence
<220> FEATURE:
<223> OTHER INFORMATION: DNA encoding fusion protein, p579

<400> SEQUENCE: 18

| | | | | | |
|---|---|---|---|---|---|
| atgtctagaa | ggccttggct | gcttgctctg | gctctggctg | ttgcacttgc | tgctggatct | 60 |
| gctggcgcct | ctacaggatc | tgatgctaca | gtgccagtgg | ccacacagga | cggccctgat | 120 |
| tatgtgtttc | acagagccca | cgagcggatg | ctgttccaga | ccagctacac | cctggaaaac | 180 |
| aacggcagcg | tgatctgcat | gcccagaggc | cagtgttact | gcgaaggctg | gctgagaagc | 240 |
| agaggcacca | gcatcgagaa | aacaatcgcc | atcactctgc | agtgggtcgt | gtttgccctg | 300 |
| tctgtggcct | gtctcggatg | gtacgcttac | caggcttgga | gagccacctg | tggctgggaa | 360 |
| gaagtgtacg | tcgccctgat | cgagatgatg | aagtccatca | tcgaggcctt | ccacgagttc | 420 |
| gacgagcctg | ccgtgatcta | cagctccaac | ggcaacaaga | ccgtgtggct | gagatatgcc | 480 |
| gagtggctgc | tgacctgtcc | tgtgatcctg | atcgccctga | gcaacctgac | cggcctgaag | 540 |
| gacgactaca | gcaagagaac | aatgggcctg | ctggtgtccg | atgtgggctg | tattgtgtgg | 600 |
| ggagccacct | ctgccatgtg | taccggatgg | accaagatcc | tgttcttcct | gatcagcctg | 660 |
| tcctacggca | tgtacaccta | cttccacgcc | gccaaagtgt | acattgaggc | ctttcacaca | 720 |
| gtgcccaagg | gcagacctag | aaccgtggtg | agaatcatgg | cttggctgtt | ctttctgagc | 780 |
| tggggcatgt | tccccgtgct | gttcgtggtg | ggccctgaag | ctttggcgt | gctgtctgtg | 840 |
| tatggctctg | ccatcggcca | cagcatcctg | gacctgatcg | ccaagaatat | gtggggcgtg | 900 |
| ctgggcaact | acctgagagt | gaagatccac | gagcacatcc | tgctgtacgg | cgacatccgg | 960 |
| aagaagacca | agatcaacgt | ggccggcgag | gagatggaag | tggagaccat | ggtggaccag | 1020 |
| gaggacgagg | ag | | | | | 1032 |

<210> SEQ ID NO 19
<211> LENGTH: 1032
<212> TYPE: DNA
<213> ORGANISM: Artificial Sequence
<220> FEATURE:
<223> OTHER INFORMATION: DNA encoding fusion protein, p580

<400> SEQUENCE: 19

| | | | | | |
|---|---|---|---|---|---|
| atgtctagaa | ggccttggct | gcttgctctg | gctctggctg | ttgcacttgc | tgctggatct | 60 |
| gctggcgcct | ctacaggatc | tgatgctaca | gtgccagtgg | ccacacagga | cggccctgat | 120 |
| tatgtgtttc | acagagccca | cgagcggatg | ctgttccaga | ccagctacac | cctggaaaac | 180 |
| aacggcagcg | tgatctgcat | gcccagaggc | cagtgttact | gcgaaggctg | gctgagaagc | 240 |
| agaggcacca | gcatcgagaa | aacaatcgcc | atcactctgc | agtgggtcgt | gtttgccctg | 300 |
| tctgtggcct | gtctcggatg | gtacgcttac | caggcttgga | gagccacctg | tggctgggaa | 360 |
| gaagtgtacg | tcgccctgat | cgagatgatg | aagtccatca | tcgaggcctt | ccacgagttc | 420 |
| gacgagcctg | ccgtgatcta | cagctccaac | ggcaacaaga | ccgtgtggct | gagatatgcc | 480 |
| gagtggctgc | tgacctgtcc | tgtgatcctg | atcaaactga | gcaacctgac | cggcctgaag | 540 |
| gacgactaca | gcaagagaac | aatgggcctg | ctggtgtccg | atgtgggctg | tattgtgtgg | 600 |
| ggagccacct | ctgccatgtg | taccggatgg | accaagatcc | tgttcttcct | gatcagcctg | 660 |
| tcctacggca | tgtacaccta | cttccacgcc | gccaaagtgt | acattgaggc | ctttcacaca | 720 |
| gtgcccaagg | gcagacctag | aaccgtggtg | agaatcatgg | cttggctgtt | ctttctgagc | 780 |
| tggggcatgt | tccccgtgct | gttcgtggtg | ggccctgaag | ctttggcgt | gctgtctgtg | 840 |

```
tatggctctg ccatcggcca cagcatcctg gacctgatcg ccaagaatat gtggggcgtg      900
ctgggcaact acctgagagt gaagatccac gagcacatcc tgctgtacgg cgacatccgg      960
aagaagacca agatcaacgt ggccggcgag gagatggaag tggagaccat ggtggaccag     1020
gaggacgagg ag                                                         1032
```

<210> SEQ ID NO 20
<211> LENGTH: 1032
<212> TYPE: DNA
<213> ORGANISM: Artificial Sequence
<220> FEATURE:
<223> OTHER INFORMATION: DNA encoding fusion protein, p581

<400> SEQUENCE: 20

```
atgtctagaa ggccttggct gcttgctctg gctctggctg ttgcacttgc tgctggatct       60
gctggcgcct ctacaggatc tgatgctaca gtgccagtgg ccacacagga cggccctgat      120
tatgtgtttc acagagccca cgagcggatg ctgttccaga ccagctacac cctggaaaac      180
aacggcagcg tgatctgcat gcccagaggc cagtgttact gcgaaggctg gctgagaagc      240
agaggcacca gcatcgagaa aacaatcgcc atcactctgc agtgggtcgt gtttgccctg      300
tctgtggcct gtctcggatg gtacgcttac caggcttgga gagccacctg tggctgggaa      360
gaagtgtacg tcgccctgat cgagatgatg aagtccatca tcgaggcctt ccacgagttc      420
gacgagcctg ccgtgatcta cagctccaac ggcaacaaga ccgtgtggct gagatatgcc      480
gagtggctgc tgacctgtcc tgtgatcctg atccgcctga gcaacctgac cggcctgaag      540
gacgactaca gcaagagaac aatgggcctg ctggtgtccg atgtgggctg tattgtgtgg      600
ggagccacct ctgccatgtg taccggatgg accaagatcc tgttcttcct gatcagcctg      660
tcctacggca tgtacaccta cttccacgcc gccaaagtgt acattgaggc ctttcacaca      720
gtgcccaagg gcagacctag aaccgtggtg agaatcatgg cttggctgtt ctttctgagc      780
tggggcatgt tccccgtgct gttcgtggtg ggccctgaag gctttggcgt gctgtctgtg      840
tatggctctg ccatcggcca cagcatcctg gacctgatcg ccaagaatat gtggggcgtg      900
ctgggcaact acctgagagt gaagatccac gagcacatcc tgctgtacgg cgacatccgg      960
aagaagacca agatcaacgt ggccggcgag gagatggaag tggagaccat ggtggaccag     1020
gaggacgagg ag                                                         1032
```

<210> SEQ ID NO 21
<211> LENGTH: 26
<212> TYPE: DNA
<213> ORGANISM: Artificial Sequence
<220> FEATURE:
<223> OTHER INFORMATION: 172G forward primer

<400> SEQUENCE: 21

```
ggactgagca acctgaccgg cctgaa                                           26
```

<210> SEQ ID NO 22
<211> LENGTH: 24
<212> TYPE: DNA
<213> ORGANISM: Artificial Sequence
<220> FEATURE:
<223> OTHER INFORMATION: Reverse primer

<400> SEQUENCE: 22

```
gatcaggatc acaggacagg tcag                                             24
```

```
<210> SEQ ID NO 23
<211> LENGTH: 26
<212> TYPE: DNA
<213> ORGANISM: Artificial Sequence
<220> FEATURE:
<223> OTHER INFORMATION: 172A forward primer

<400> SEQUENCE: 23
gccctgagca acctgaccgg cctgaa                                          26

<210> SEQ ID NO 24
<211> LENGTH: 26
<212> TYPE: DNA
<213> ORGANISM: Artificial Sequence
<220> FEATURE:
<223> OTHER INFORMATION: 172K forward primer

<400> SEQUENCE: 24
aaactgagca acctgaccgg cctgaa                                          26

<210> SEQ ID NO 25
<211> LENGTH: 26
<212> TYPE: DNA
<213> ORGANISM: Artificial Sequence
<220> FEATURE:
<223> OTHER INFORMATION: 172R forward primer

<400> SEQUENCE: 25
cgcctgagca acctgaccgg cctgaa                                          26
```

MODIFIED CHANNELRHODOPSIN

TECHNICAL FIELD

The present invention relates to a modified channelrhodopsin. More specifically, it relates to a modified channelrhodopsin having high ion permeability (photoreactivity).

BACKGROUND ART

It is well known that a research aiming at reconstruction of visual function by optogenetics to control cellular response by applying light to neurons made to express a photosensitive protein (channelrhodopsin) by gene transfer has been globally performed, and the present inventors also have reported a modified channelrhodopsin whose expression efficiency on a cell membrane is improved by substituting an N-terminal region of a Volvox carteri-derived channelrhodopsin by an N-terminal region of a *Chlamydomonas reinhardtii*-derived channelrhodopsin-1 in Patent Document 1. The modified channelrhodopsin can induce depolarization by opening an ion channel through application of light, and the present inventors have succeeded in restoring eyesight by introducing a gene thereof into the retina of a rat with visual loss.

However, a modified channelrhodopsin having higher ion permeability than a previously reported modified channelrhodopsin has been demanded.

PRIOR ART DOCUMENTS

Patent Document

Patent Document 1: Japanese Patent No. 5322067

SUMMARY OF THE INVENTION

Problems that the Invention is to Solve

Therefore, an object of the present invention is to provide a modified channelrhodopsin having high ion permeability.

Means for Solving the Problems

As a result of intensive studies in view of the above points, the present inventors have found that a channelrhodopsin having high ion permeability is obtained by substituting the third extracellular domain counted from the N-terminal side of three extracellular domains included in a Volvox carteri-derived channelrhodopsin by a corresponding extracellular domain of a *Chlamydomonas reinhardtii*-derived channelrhodopsin-2.

A modified channelrhodopsin of the present invention achieved based on the above-mentioned findings is, in a first embodiment, a polypeptide obtained by substituting the third extracellular domain counted from the N-terminal side of three extracellular domains included in a Volvox carteri-derived channelrhodopsin by a corresponding extracellular domain of a *Chlamydomonas reinhardtii*-derived channelrhodopsin-2.

Further, a modified channelrhodopsin is, in a second embodiment, the modified channelrhodopsin of the first embodiment, in which the Volvox carteri-derived channelrhodopsin contains at least amino acids at positions 67 to 322 in the amino acid sequence represented by SEQ ID NO: 1.

Further, a modified channelrhodopsin is, in a third embodiment, the modified channelrhodopsin of the second embodiment, which is obtained by substituting amino acids at positions 142 to 169 in the amino acid sequence represented by SEQ ID NO: 1 by amino acids at positions 143 to 170 in the amino acid sequence of a *Chlamydomonas reinhardtii*-derived channelrhodopsin-1 represented by SEQ ID NO: 2.

Further, a modified channelrhodopsin is, in a fourth embodiment, the modified channelrhodopsin of the third embodiment 3, which is any of the following (a) to (c):
  (a) a polypeptide composed of the amino acid sequence represented by SEQ ID NO: 4;
  (b) a polypeptide that is composed of an amino acid sequence including deletion, substitution, addition, or insertion of one or a plurality of amino acids in the amino acid sequence represented by SEQ ID NO: 4, and that has a channelrhodopsin function; and
  (c) a polypeptide that is composed of an amino acid sequence having at least 90% sequence identity to the amino acid sequence represented by SEQ ID NO: 4, and that has a channelrhodopsin function.

Further, a modified channelrhodopsin is, in a fifth embodiment, the modified channelrhodopsin of the fourth embodiment, which is a polypeptide composed of the amino acid sequence represented by SEQ ID NO: 8.

Further, a modified channelrhodopsin is, in a sixth embodiment, the modified channelrhodopsin of any one of the first to third embodiments, which is obtained by substituting the sixth transmembrane domain counted from the N-terminal side of seven transmembrane domains included in the Volvox carteri-derived channelrhodopsin by a corresponding transmembrane domain of a Chloromonas oogama-derived channelrhodopsin.

Further, a modified channelrhodopsin is, in a seventh embodiment, the modified channelrhodopsin of the second or third embodiment, which is obtained by substituting amino acids at position 323 and downstream thereof in the amino acid sequence represented by SEQ ID NO: 1 by amino acids at position 265 and downstream thereof in the amino acid sequence of a Chloromonas oogama-derived channelrhodopsin represented by SEQ ID NO: 5.

Further, a modified channelrhodopsin is, in an eighth embodiment, the modified channelrhodopsin of the sixth or seventh embodiment, which is any of the following (a) to (c):
  (a) a polypeptide composed of the amino acid sequence represented by SEQ ID NO: 6;
  (b) a polypeptide that is composed of an amino acid sequence including deletion, substitution, addition, or insertion of one or a plurality of amino acids in the amino acid sequence represented by SEQ ID NO: 6, and that has a channelrhodopsin function; and
  (c) a polypeptide that is composed of an amino acid sequence having at least 90% sequence identity to the amino acid sequence represented by SEQ ID NO: 6, and that has a channelrhodopsin function.

Further, a modified channelrhodopsin is, in a ninth embodiment, the modified channelrhodopsin of the eighth embodiment, which is a polypeptide obtained by substituting His at position 172 in the polypeptide composed of the amino acid sequence represented by SEQ ID NO: 6 by another amino acid.

Further, a modified channelrhodopsin is, in a tenth embodiment, the modified channelrhodopsin of the ninth embodiment, which is a polypeptide composed of the amino acid sequence represented by any of SEQ ID NOS: 9 to 12.

Further, a modified channelrhodopsin is, in an eleventh embodiment, the modified channelrhodopsin of the sixth or seventh embodiment, which is any of the following (a) to (c):
- (a) a polypeptide composed of the amino acid sequence represented by SEQ ID NO: 7;
- (b) a polypeptide that is composed of an amino acid sequence including deletion, substitution, addition, or insertion of one or a plurality of amino acids in the amino acid sequence represented by SEQ ID NO: 7, and that has a channelrhodopsin function; and
- (c) a polypeptide that is composed of an amino acid sequence having at least 90% sequence identity to the amino acid sequence represented by SEQ ID NO: 7, and that has a channelrhodopsin function.

Further, a polynucleotide in a twelfth embodiment of the present invention encodes the polypeptide of any one of the first to eleventh embodiments.

Further, an expression vector in a thirteenth embodiment of the present invention includes the polynucleotide of the twelfth embodiment functionally linked to a promoter.

Further, a cell in a fourteenth embodiment of the present invention expresses the polypeptide of any one of the first to eleventh embodiments.

Further, a cell in a fifteenth embodiment of the present invention is the cell of the fourteenth embodiment, in which the cell is a neuron.

Further, a sixteenth embodiment of the present invention is directed to use of any one of the polypeptides of the first to eleventh embodiments, the polynucleotide of the twelfth embodiment and the expression vector of the thirteenth embodiment in the production of a pharmaceutical for treating a subject suffering from damage to the outer retinal layers.

Further, a seventeenth embodiment of the present invention is the use in the sixteenth embodiment, in which the damage to the outer retinal layers is retinitis pigmentosa, age-related macular degeneration, or retinal detachment.

Further, an eighteenth embodiment of the present invention is a pharmaceutical composition for treating damage to the outer retinal layers of the present invention, which contains either the polypeptide of any one of the first to eleventh embodiments or the expression vector of the thirteenth embodiment as an active ingredient.

Effect of the Invention

According to the present invention, a modified channelrhodopsin having high ion permeability can be provided.

BRIEF DESCRIPTION OF THE DRAWINGS

FIG. 1 A structure of the plasmid for preparing an adeno-associated virus vector expressing p525 in Example 1.

FIG. 2 A graph showing that p525, p548, and p550 have higher ion permeability than mVChR1 in Test Example 1.

FIG. 3 A graph showing the ion permeability of p578, p579, p580, and p581 in Test Example 4.

FIG. 4 A graph showing that p579 shows a shorter τon than p548 in Test Example 5.

FIG. 5 A graph showing that p579 shows a shorter τoff than p548 in Test Example 5.

FIG. 6 A graph showing that the visually evoked potential can be recorded by introducing the p548 gene into the retina in Test Example 6.

FIG. 7 A photograph indicating that the expression of p548 can be confirmed in the entire neural retina when a retinal flat-mount preparation is observed under a fluorescence microscope in Test Example 6.

FIG. 8 Photographs indicating that the expression of p548 can be confirmed mainly in the retinal ganglion cell layer when a retinal section preparation is observed under a fluorescence microscope in Test Example 6.

MODE FOR CARRYING OUT THE INVENTION

A modified channelrhodopsin of the present invention is a polypeptide obtained by substituting the third extracellular domain counted from the N-terminal side of three extracellular domains included in a Volvox carteri-derived channelrhodopsin by a corresponding extracellular domain of a *Chlamydomonas reinhardtii*-derived channelrhodopsin-2.

As a specific example of the Volvox carteri-derived channelrhodopsin, a polypeptide containing at least amino acids at positions 67 to 322 in the amino acid sequence represented by SEQ ID NO: 1 is exemplified. The polypeptide composed of the amino acid sequence represented by SEQ ID NO: 1 is a modified channelrhodopsin reported in Patent Document 1 by the present inventors (a polypeptide composed of the amino acid sequence represented by SEQ ID NO: 10 in Patent Document 1). This modified channelrhodopsin is a polypeptide composed of 344 amino acids, in which the expression efficiency on a cell membrane is improved by substituting an N-terminal region of a Volvox carteri-derived channelrhodopsin by an N-terminal region of a *Chlamydomonas reinhardtii*-derived channelrhodopsin-1 (which is a region involved in cell membrane-localized expression and includes no transmembrane domain). The amino acids at positions 1 to 66 in the amino acid sequence represented by SEQ ID NO: 1 are amino acids at positions 1 to 66 in the amino acid sequence of a *Chlamydomonas reinhardtii*-derived channelrhodopsin-1 represented by SEQ ID NO: 2. In the present invention, the modified channelrhodopsin which is a polypeptide composed of the amino acid sequence represented by SEQ ID NO: 1 is referred to as "mVChR1". Further, the matters described in Patent Document 1 are treated as matters described in the present description.

The amino acid sequence of mVChR1 represented by SEQ ID NO: 1 is as follows. The third extracellular domain (EX3) counted from the N-terminal side of three extracellular domains included in mVChR1 is Gly271 to Ser279.

(Amino Acid Sequence of mVChR1)

MSRRPWLLALALAVALAAGSAGASTGSDATVPVATQDGPD YVFHRAHER

MLFQTSYTLENNGSVICMPRGQCYCEGWLRSRGTSIEKTIAITLQWVVFA
                                              TM1

LSVACLGWYAYQAWRATCGWEEVYVALIEMMKSIIEAFIIEFDSPATLWL
         IN1        TM2                    EX1

SSGNGVVWMRYGEWLLTCPVLLIHLSNLTGLKDDYSKRTMGLLVSDVGCI
      TM3                IN2          TM4

VWGATSAMCTGWTKILFFLISLSYGMYTYFHAAKVYIEAPHTVPKGICRE
    EX2TM5                              IN3   TM6

LVRVMAWTFFVAWGMFPVLFLLGTEGFGHISPYGSAIGHSILDLIAKNMW
                             EX3     TM7

GVLGNYLRVKTHEHILLYGDIRKKQKITIAGQEMEVETLVAEEEDR

※ TM: transmembrane domain
   IN: intracellular domain
   EX: extracellular domain The modified channelrhodopsin of the present invention is, when taking mVChR1 as an example, a polypeptide obtained by substituting the above-mentioned EX3 by a corresponding extracellular domain of a *Chlamydomonas reinhardtii*-derived channelrhodopsin-2, that is, the third extracellular domain counted from the N-terminal side of three extracellular domains included in the *Chlamydomonas reinhardtii*-derived channelrhodopsin-2. The amino acid sequence of the *Chlamydomonas reinhardtii*-derived channelrhodopsin-2 is as represented by SEQ ID NO: 3, and the third extracellular domain counted from the N-terminal side thereof is Gly233 to Ser241. With the substitution of EX3, the transmembrane domain upstream or downstream of EX3, that is, an amino acid (s) at the C-terminal side of TM6 adjacent to the N-terminus of EX3 and/or an amino acid(s) at the N-terminal side of TM7 adjacent to the C-terminus of EX3 may be substituted together, but the number of amino acids that may be substituted is preferably 3 at the maximum. Substitution of more than 3 amino acids may affect the function of the transmembrane domain.

The modified channel rhodopsin of the present invention may be a polypeptide obtained by further modifying another domain or region in addition to having undergone substitution of the third extracellular domain counted from the N-terminal side of three extracellular domains included in the Volvox carteri-derived channelrhodopsin by a corresponding extracellular domain of the *Chlamydomonas reinhardtii*-derived channelrhodopsin-2. For example, when taking mVChR1 as an example, it may be a polypeptide obtained by substituting amino acids at positions 142 to 169 in the amino acid sequence represented by SEQ ID NO: 1 by amino acids at positions 143 to 170 in the amino acid sequence of a *Chlamydomonas reinhardtii*-derived channelrhodopsin-1 represented by SEQ ID NO: 2.

As a specific example of such a modified channelrhodopsin, a polypeptide composed of the amino acid sequence represented by SEQ ID NO: 4 is exemplified. This polypeptide (p525) is configured by substituting EX3 of mVChR1 by a corresponding extracellular domain of the *Chlamydomonas reinhardtii*-derived channelrhodopsin-2, and also substituting amino acids at positions 142 to 169 in mVChR1 by amino acids at positions 143 to 170 in the *Chlamydomonas reinhardtii*-derived channelrhodopsin-1 represented by SEQ ID NO: 2 (note that with the substitution of EX3, Pro at position 280 in TM7 is substituted by Val).

Further, the modified channelrhodopsin of the present invention may be, for example, when taking mVChR1 as an example, a polypeptide obtained by substituting the sixth transmembrane domain (TM6) counted from the N-terminal side thereof by a corresponding transmembrane domain of a Chloromonas oogama-derived channelrhodopsin. The amino acid sequence of the Chloromonas oogama-derived channelrhodopsin is as represented by SEQ ID NO: 5, and the sixth transmembrane domain counted from the N-terminal side thereof is Arg187 to Val212.

Further, the modified channelrhodopsin of the present invention may be, for example, when taking mVChR1 as an example, a polypeptide obtained by substituting amino acids at position 323 and downstream thereof in the amino acid sequence represented by SEQ ID NO: 1 by amino acids at position 265 and downstream thereof in the amino acid sequence of the Chloromonas oogama-derived channelrhodopsin represented by SEQ ID NO: 5.

As a specific example of such a modified channelrhodopsin, a polypeptide composed of the amino acid sequence represented by SEQ ID NO: 6 is exemplified. This polypeptide (p548) is configured by substituting EX3 of mVChR1 by a corresponding extracellular domain of the *Chlamydomonas reinhardtii*-derived channelrhodopsin-2, and also substituting amino acids at positions 142 to 169 in mVChR1 by amino acids at positions 143 to 170 in *Chlamydomonas reinhardtii*-derived channelrhodopsin-1 represented by SEQ ID NO: 2, and further substituting TM6 of mVChR1 by a corresponding transmembrane domain of the Chloromonas oogama-derived channelrhodopsin, and substituting amino acids at positions 323 to 344 in mVChR1 by amino acids at positions 265 to 286 in the Chloromonas oogama-derived channelrhodopsin represented by SEQ ID NO: 5 (note that with the substitution of EX3, Pro at position 280 in TM7 is substituted by Val).

As another specific example, a polypeptide composed of the amino acid sequence represented by SEQ ID NO: 7 is exemplified. This polypeptide (p550) is configured by substituting EX3 of mVChR1 by a corresponding extracellular domain of the *Chlamydomonas reinhardtii*-derived channelrhodopsin-2, and also substituting amino acids at positions 142 to 169 in mVChR1 by amino acids at positions 143 to 170 in the *Chlamydomonas reinhardtii*-derived channelrhodopsin-1 represented by SEQ ID NO: 2, and further substituting TM6 of mVChR1 by a corresponding transmembrane domain of the Chloromonas oogama-derived channelrhodopsin, and substituting amino acids at positions 323 to 344 in mVChR1 by amino acids at positions 265 to 286 in the Chloromonas oogama-derived channelrhodopsin represented by SEQ ID NO: 5, which is the same as the polypeptide (p548) composed of the amino acids sequence represented by SEQ ID NO: 6 described above, and in addition thereto, further deleting amino acids at positions 28 to 60 in mVChR1 (note that with the substitution of EX3, Pro at position 280 in TM7 is substituted by Val).

The modified channelrhodopsin of the present invention includes a polypeptide that includes deletion, substitution, addition, or insertion of one or a plurality of amino acids in the amino acid sequence represented by each of SEQ ID NOS: 4, 6, and 7, and that has a channelrhodopsin function. Further, it includes a polypeptide that is composed of an amino acid sequence having at least 90% sequence identity to the amino acid sequence represented by each of SEQ ID NOS: 4, 6, and 7, and that has a channelrhodopsin function. Here, the "a plurality of" is an integer of 50 or less, preferably an integer of 30 or less, more preferably an integer of 10 or less, and, for example, 2 to 9, 2 to 7, or 2 to 5. The sequence identity to the amino acid sequence represented by each of SEQ ID NOS: 4, 6, and 7 is preferably at least 91%, more preferably at least 92%, more preferably at least 93%, more preferably at least 94%, more preferably at least 95%, more preferably at least 96%, more preferably at least 97%, more preferably at least 98%, and most preferably at least 99%. Note that the % of the identity refers to a value calculated using a software for calculating the identity between a plurality of (two) amino acid sequences (e.g., FASTA, DANASYS, BLAST, etc.) with default settings. As a specific example of such a modified channelrhodopsin, a polypeptide (p528) composed of the amino acid sequence represented by SEQ ID NO: 8, which is obtained by substitution of Trp at position 210 in the polypeptide composed of the amino acid sequence represented by SEQ ID NO: 4 by Tyr and substitution of Thr at position 211 by Val, is exemplified. Further, a polypeptide obtained by substitution of His at position 172 in the polypeptide composed of the amino acid sequence represented by each of SEQ ID NOS: 4, 6, and 8, or at position 139 in the polypeptide composed of the amino acid sequence represented by SEQ ID NO: 7 by another amino acid, for example, Gly, Ala, Lys, Arg, or the like, specifically, a polypeptide (p578) composed of the amino acid sequence represented by SEQ ID NO: 9, which is obtained by substitution of His at position 172 in the polypeptide composed of the amino acid sequence represented by SEQ ID NO: 6 by Gly, a polypeptide (p579) composed of the amino acid sequence represented by SEQ ID NO: 10, which is obtained by substitution thereof by Ala, a polypeptide (p580) composed of the amino acid sequence represented by SEQ ID NO: 11, which is obtained by substitution thereof by Lys, a polypeptide (p581) composed of the amino acid sequence represented by SEQ ID NO: 12, which is obtained by substitution thereof by Arg, and the like are exemplified. The substitution of His at position 172 in the polypeptide composed of the amino acid sequence represented by each of SEQ ID NOS: 4, 6, and 8, or at position 139 in the polypeptide composed of the amino acid sequence represented by SEQ ID NO: 7 by another amino acid can bring about a change in at least one of the time until the channel opens from the start of light irradiation (opening speed: τon) and the time until the channel closes from the stop of light irradiation (closing speed: τoff). Note that the "has a channelrhodopsin function" means to have a channel function to control ion permeability between the outside and the inside of a cell by sensing light, which is well known to those skilled in the art, and it is preferred that at least one of the biological activities evaluated by the degree of light sensitivity, the light sensitive wavelength, the degree of ion permeability, τon, τoff, or the like is at least equivalent to the biological activity of the polypeptide composed of the amino acid sequence represented by each of SEQ ID NOS: 4, 6, 7, and 8.

The modified channelrhodopsin of the present invention can be produced by a genetic engineering technique. Specifically, first, a polynucleotide encoding the modified channelrhodopsin of the present invention (hereinafter, referred to as "the modified channelrhodopsin gene of the present invention") is prepared. The modified channelrhodopsin gene of the present invention can be prepared by a method known to those skilled in the art. Specifically, for example, the gene can be prepared by chemical synthesis based on the sequence information of each of a polynucleotide encoding the modified channelrhodopsin reported by the present inventors in Patent Document 1, a polynucleotide encoding a *Chlamydomonas reinhardtii*-derived channelrhodopsin-2, and further if needed, a polynucleotide encoding a *Chlamydomonas reinhardtii*-derived channelrhodopsin-1, and a polynucleotide encoding a Chloromonas oogama-derived channelrhodopsin. Further, the gene can also be prepared by amplifying a desired region of each of the polynucleotides using PCR primers that amplify the desired region of each of the polynucleotides based on the sequence information of each of the polynucleotides, and linking these regions using, for example, Gibson Assembly System (New England Biolabs Ltd.) or the like. Subsequently, the modified channelrhodopsin gene of the present invention functionally linked to a promoter is integrated into an expression vector that can maintain replication in a host bacterial cell, can stably express the encoded polypeptide, and can stably maintain the gene, a host is transformed using the obtained recombinant expression vector, and the modified channelrhodopsin of the present invention can be produced in the host. For the recombination technique, Proc. Natl. Acad. Sci. USA., 1984 81: 5662, or Molecular Cloning: A Laboratory Manual (1989) Second Edition, Cold Spring Harbor Laboratory Press, or the like can be referred to. As the expression vector, *Escherichia coli*-derived plasmids (e.g., pET28, pGEX4T, pUC118, pUC119, pUC18, pUC19, and other plasmid DNAs), *Bacillus subtilis*-derived plasmids (e.g., pUB110, pTP5, and other plasmid DNAs), yeast-derived plasmids (e.g., YEp13, YEp24, YCp50, and other plasmid DNAs), λ phages (λgt11 and λZAP), plasmids for use in mammals (pCMV and pSV40), virus vectors (e.g., animal virus vectors such as adenovirus vectors, adeno-associated virus vectors, retrovirus vectors, lentivirus vectors, or vaccinia virus vectors, and insect virus vectors such as baculovirus vectors), vectors for use in plants (e.g., binary vector pBI series), cosmid vectors, and the like can be used. Here, the "functionally linked" refers to a functional bond between a promoter sequence and a target polynucleotide sequence such that the promoter sequence can start transcription of the target polynucleotide sequence. The promoter is not particularly limited, and a suitable promoter may only be selected according to the host, and a known constitutive promoter or an inducible promoter can be used, but a constitutive promoter is preferably used. Specific examples thereof include CMV promoter, SV40 promoter, CAG promoter, synapsin promoter, rhodopsin promoter, CaMV promoter, glycolytic enzyme promoter, lac promoter, trp promoter, tac promoter, GAPDH promoter, GAL1 promoter, PH05 promoter, PGK promoter, thy1 promoter, GRK promoter, and RPEJ promoter. For the purpose of specifically expressing the modified channelrhodopsin of the present invention in a specific cell, a transcriptional regulatory domain of a polypeptide gene specifically expressed in the cell (for example, a transcriptional regulatory domain of IRBP (Interphotoreceptor retinoid binding protein) which is specifically expressed in a photoreceptor cell (Marjorie Nicoud et al., The Journal of Gene Medicine, Volume 9, Issue 12, 1013-1107, December 2007)) may be linked upstream of such a promoter. The insertion of the modified channelrhodopsin gene of the present invention into an expression vector is carried out, for example, by creating or linking a restriction enzyme site flanking the modified channelrhodopsin gene of the present invention, and inserting the resultant into a restriction enzyme site or a multicloning site of a suitable vector DNA. The expression vector may include, in addition to a promoter and the modified channelrhodopsin gene of the present invention, an enhancer and other cis elements, a splicing signal, a polyA addition signal, a selection marker (a drug resistance gene marker such as an ampicillin resistance marker or a tetracycline resistance marker, an auxotrophic complementary gene marker such as LEU1, TRP1, or URA3, a dominant selection marker such as APH, DHFR, or TK, etc.), a ribosome binding site (RBS), or the like as needed. The transformation of the host can be carried out using a protoplast method, a spheroplast method, a competent cell method, a virus method, a calcium phosphate method, a lipofection method, a microinjection method, a gene bombardment method, an *agrobacterium* method, electroporation, or the like. The thus obtained transformant is cultured under appropriate conditions using a medium containing an assimilable carbon source, a nitrogen source, a metal salt, a vitamin, or the like. The culture of the transformant is usually carried out under aerobic conditions such as shake culture or aerated and agitated culture at 25 to 37° C. for 3 to 6 hours. The pH is kept around neutral during the period of culture. The pH is adjusted using an inorganic or organic acid, an alkaline solution, or the like. During the culture, an antibiotic such as ampicillin or tetracycline may be added to the medium according to the selection marker inserted into the recombinant expression vector as needed. Further, the host used for the transformation is not particularly limited as long as it can express the modified channelrhodopsin of the present invention, and examples thereof include bacteria (*Escherichia coli* and *Bacillus subtilis*), yeasts (*Saccharomyces cerevisiae*, etc.), animal cells (COS cells, Chinese hamster ovary (CHO) cells, 3T3 cells, BHK cells, HEK 293 cells, etc.), and insect cells. The modified channelrhodopsin of the present invention can be obtained in the form of retaining its activity by fractionation or purification using a common method from a culture (a culture supernatant, cultured cells, cultured bacterial cells, a homogenate of cells or bacterial cells, or the like) obtained by culturing the transformant, followed by ultrafiltration concentration, lyophilization, spray drying, crystallization, or the like. Alternatively, the modified channelrhodopsin of the present invention may be provided in the form of cells expressing the modified channelrhodopsin of the present invention without performing isolation or purification. In that case, the host cells used for the transformation are host cells suitable for subsequent use, for example, neurons (photoreceptor cells, bipolar cells, ganglion cells, etc.), preferably human neurons. Further, when the modified channelrhodopsin of the present invention is used for a medical application, it may be provided in the form of an expression vector for the modified channelrhodopsin of the present invention. In that case, it is preferred to use an expression vector having excellent introduction efficiency into cells, replication maintenance in cells, stability, expression efficiency, and the like. Examples of such a vector can include virus vectors such as an adeno-associated virus vector, a retrovirus vector, and a lentivirus vector, (autonomously replicable) plasmids, and transposons. The plasmid for preparing an expression vector for the modified channelrhodopsin of the present invention can be prepared according to the method described, for example, in Tomita H et al., Invest Ophthalmol Vis Sci. 2007 August; 48(8): 3821-6, or Sugano E et al., Invest Ophthalmol Vis Sci. 2005 September; 46(9): 3341-8.

Here, examples of the modified channelrhodopsin gene of the present invention include a polynucleotide composed of the nucleotide sequence represented by SEQ ID NO: 13 (encoding a polypeptide composed of the amino acid sequence represented by SEQ ID NO: 4), a polynucleotide composed of the nucleotide sequence represented by SEQ ID NO: 14 (encoding a polypeptide composed of the amino acid sequence represented by SEQ ID NO: 6), a polynucleotide composed of the nucleotide sequence represented by SEQ ID NO: 15 (encoding a polypeptide composed of the amino acid sequence represented by SEQ ID NO: 7), a polynucleotide composed of the nucleotide sequence represented by SEQ ID NO: 16 (encoding a polypeptide composed of the amino acid sequence represented by SEQ ID NO: 8), a polynucleotide composed of the nucleotide sequence represented by SEQ ID NO: 17 (encoding a polypeptide composed of the amino acid sequence represented by SEQ ID NO: 9), a polynucleotide composed of the nucleotide sequence represented by SEQ ID NO: 18 (encoding a polypeptide composed of the amino acid sequence represented by SEQ ID NO: 10), a polynucleotide composed of the nucleotide sequence represented by SEQ ID NO: 19 (encoding a polypeptide composed of the amino acid sequence represented by SEQ ID NO: 11), and a polynucleotide composed of the nucleotide sequence represented by SEQ ID NO: 20 (encoding a polypeptide composed of the amino acid sequence represented by SEQ ID NO: 12). However, the modified channelrhodopsin gene of the present invention is not limited to these polynucleotides, and includes a polynucleotide that hybridizes to a complementary strand of each of these polynucleotides under stringent conditions and encodes a polypeptide having a channelrhodopsin function. Further, the gene includes a polynucleotide that has at least 90%, preferably at least 91%, more preferably at least 92%, more preferably at least 93%, more preferably at least 94%, more preferably at least 95%, more preferably at least 96%, more preferably at least 97%, more preferably at least 98%, and most preferably at least 99% sequence identity to the nucleotide sequence represented by each of SEQ ID NOS: 13 to 20 and that encodes a polypeptide having a channelrhodopsin function. Here, the "hybridization under stringent conditions" includes, for example, hybridization in 3 to 4×SSC (150 mM sodium chloride, 15 mM sodium citrate, pH 7.2) and 0.1 to 0.5% SDS at 30 to 50° C. for 1 to 24 hours, preferably hybridization in 3.4×SSC and 0.3% SDS at 40 to 45° C. for 1 to 24 hours, and subsequent washing. As washing conditions, for example, conditions such as continuous washing with a solution containing 2×SSC and 0.1% SDS, a 1×SSC solution, and a 0.2×SSC solution at room temperature are exemplified. However, the combination of the above conditions is exemplary, and those skilled in the art can achieve the same stringency as described above by properly combining the above or other factors determining hybridization stringency (for example, the concentration, length, and GC content of a hybridization probe, the reaction time of hybridization, etc.).

The modified channelrhodopsin of the present invention maintains the property of the modified channelrhodopsin (for example, mVChR1) described in Patent Document 1 that the expression efficiency on a cell membrane is high, and moreover has a property that the ion permeability is high, when it is a polypeptide obtained by substituting an N-terminal region of a Volvox carteri-derived channelrhodopsin by an N-terminal region of a *Chlamydomonas reinhardtii*-derived channelrhodopsin-1 according to Patent Document 1. Therefore, the modified channelrhodopsin of the present invention and an expression vector including a polynucleotide encoding the modified channelrhodopsin are useful for treating a subject suffering from damage to the outer retinal layers. Here, the "damage to the outer retinal layers" refers to any disease in which cells other than photoreceptor cells remain normal or retain some of their functions although visual dysfunction or visual function impairment has occurred as by the degeneration or loss of photoreceptor cells present in the outer retinal layers. As such a disease, retinitis pigmentosa, age-related macular degeneration, retinal detachment, and the like can be exemplified. The "subject" means a subject with visual loss or a subject at risk for visual loss due to damage to the outer retinal layers. The subject is not limited to a human and may be any other mammal. Examples of such other mammal include mice, rats, monkeys, rabbits, dogs, cats, cattle, and horses. The "treatment of a subject suffering from damage to the outer retinal layers" means recovery of visual function as compared to before administration of the pharmaceutical of the present invention in a subject with visual loss or at risk for visual loss due to damage to the outer retinal layers.

The pharmaceutical composition of the present invention contains the modified channelrhodopsin of the present invention or the expression vector including a polynucleotide encoding the modified channelrhodopsin as an active ingredient, and is formulated as a pharmaceutical for treating a subject suffering from damage to the outer retinal layers. The effective dose thereof is an amount that can have a therapeutic effect on a given symptom or usage, and is properly determined by those skilled in the art based on implementation of a test using an animal or a clinical test, however, the age, body weight, and sex of the subject being an administration target, the condition or severity of the disease, the administration method, and the like are considered. In the case of a virus, the viral dose is, for example, $10^{12}$ to $10^{12}$ capsids/ml (e.g., about $10^{13}$ capsids/ml). In the formulation as a pharmaceutical, the active ingredient may be formulated together with one or more pharmaceutically acceptable carriers. Examples of the pharmaceutically acceptable carrier include various buffer solutions, for example, saline and buffer solutions of phosphates, acetates, and the like. The pharmaceutical may contain another therapeutic ingredient. Examples of the another therapeutic ingredient include agents known as therapeutic agents for retinitis pigmentosa, age-related macular degeneration, retinal detachment, or the like. The pharmaceutical can be formulated, for example, into an injection for local administration, an eye drop, an eye wash, or the like. An injectable preparation can be provided, for example, as an ample or in a unit dosage form in a container for multiple administrations, by adding a preservative. Further, the pharmaceutical may be in the form of a lyophilized preparation to be reconstituted before use with a suitable vehicle, for example, pyrogen-free sterile water or the like. The pharmaceutical is preferably administered by direct injection into the affected area of a subject, that is, the retina, or direct contact with the vitreous body.

EXAMPLES

Hereinafter, the present invention will be described in detail by way of Examples, however, the present invention should not be construed as being limited to the following description.

Example 1: Modified Channelrhodopsin of Present Invention Composed of Amino Acid Sequence Represented by SEQ ID NO: 4 (Acquisition of Cells Expressing p525)

A polynucleotide, in which a region of a polynucleotide encoding amino acids at positions 1 to 141 in the amino acid sequence represented by SEQ ID NO: 1 of mVChR1 described in Patent Document 1, a region of a polynucleotide encoding amino acids at positions 143 to 170 in the amino acid sequence represented by SEQ ID NO: 2 of a *Chlamydomonas reinhardtii*-derived channelrhodopsin-1, a region of a polynucleotide encoding amino acids at positions 170 to 270 in the amino acid sequence represented by SEQ ID NO: 1, a region of a polynucleotide encoding amino acids at positions 233 to 242 in the amino acid sequence represented by SEQ ID NO: 3 of a *Chlamydomonas reinhardtii*-derived channelrhodopsin-2, and a region of a polynucleotide encoding amino acids at positions 280 to 342 in the amino acid sequence represented by SEQ ID NO: 1 were linked, and a restriction enzyme sequence was added to the 5' end and the 3' end thereof, was chemically synthesized and inserted into a multicloning site of the plasmid for preparing an adeno-associated virus vector. The structure of the thus prepared plasmid for preparing an adeno-associated virus vector expressing p525 is shown in FIG. 1. In the plasmid, a fluorescent protein gene (venus) is located in a 3' region of the multicloning site, and the target gene is expressed in the form of a fusion protein with venus attached to a C-terminal region. Therefore, this plasmid was transfected into cells by a calcium phosphate method, and a cell expressing p525 was specified using venus as an index. Specifically, to a tube containing a solution of the plasmid (the plasmid amount: 15 μg), 1.5 mL of 0.3 M $CaCl_2$ was added, followed by stirring by inversion, and then, the content was added to 1.5 mL of 2×HBS (280 mM NaCl, 1.5 mM $Na_2HPO_4$, 50 mM HEPES, pH 7.1) provided in another tube. The resultant was again stirred by inversion, and then added dropwise to HEK (Human Embryonic Kidney) 293 cells as a human embryonic kidney-derived cell line cultured in DMEM medium containing 10% FBS to transfect the plasmid, and the cells were cultured at 37° C. and 5% $CO_2$. After 6 hours, the medium was replaced with a fresh medium, and the cells were cultured for 2 days, and then, the cells were observed under a fluorescence microscope, thereby confirming the expression of p525 in the cells.

Example 2: Modified Channelrhodopsin of Present Invention Composed of Amino Acid Sequence Represented by SEQ ID NO: 6 (Acquisition of Cells Expressing p548)

The cells expressing p548 were prepared in the same manner as in Example 1 except that a polynucleotide, in which a region of a polynucleotide encoding amino acids at positions 1 to 141 in the amino acid sequence represented by SEQ ID NO: 1 of mVChR1 described in Patent Document 1, a region of a polynucleotide encoding amino acids at positions 143 to 170 in the amino acid sequence represented by SEQ ID NO: 2 of a *Chlamydomonas reinhardtii*-derived channelrhodopsin-1, a region of a polynucleotide encoding amino acids at positions 170 to 244 in the amino acid sequence represented by SEQ ID NO: 1, a region of a polynucleotide encoding amino acids at positions 187 to 212 in the amino acid sequence represented by SEQ ID NO: 5 of a Chloromonas oogama-derived channelrhodopsin, a region of a polynucleotide encoding amino acids at positions 233 to 242 in the amino acid sequence represented by SEQ ID NO: 3 of a *Chlamydomonas reinhardtii*-derived channelrhodopsin-2, a region of a polynucleotide encoding amino acids at positions 280 to 322 in the amino acid sequence represented by SEQ ID NO: 1, and a region of a polynucleotide encoding amino acids at positions 265 to 286 in the amino acid sequence represented by SEQ ID NO: 5 were linked, and a restriction enzyme sequence was added to the 5' end and the 3' end thereof, was chemically synthesized and inserted into a multicloning site of the plasmid for preparing an adeno-associated virus vector.

Example 3: Modified Channelrhodopsin of Present Invention Composed of Amino Acid Sequence Represented by SEQ ID NO: 7 (Acquisition of Cells Expressing p550)

The cells expressing p550 were prepared in the same manner as in Example 1 except that a polynucleotide, in which a region of a polynucleotide encoding amino acids at positions 1 to 27 in the amino acid sequence represented by SEQ ID NO: 1 of mVChR1 described in Patent Document 1, a region of a polynucleotide encoding amino acids at positions 61 to 141 in the amino acid sequence represented by SEQ ID NO: 1, a region of a polynucleotide encoding amino acids at positions 143 to 170 in the amino acid sequence represented by SEQ ID NO: 2 of a *Chlamydomonas reinhardtii*-derived channelrhodopsin-1, a region of a polynucleotide encoding amino acids at positions 170 to 244 in the amino acid sequence represented by SEQ ID NO: 1, a region of a polynucleotide encoding amino acids at positions 187 to 212 in the amino acid sequence represented by SEQ ID NO: 5 of a Chloromonas oogama-derived channelrhodopsin, a region of a polynucleotide encoding amino acids at positions 233 to 242 in the amino acid sequence represented by SEQ ID NO: 3 of a *Chlamydomonas reinhardtii*-derived channelrhodopsin-2, a region of a polynucleotide encoding amino acids at positions 280 to 322 in the amino acid sequence represented by SEQ ID NO: 1, and a region of a polynucleotide encoding amino acids at positions 265 to 286 in the amino acid sequence represented by SEQ ID NO: 5 were linked, and a restriction enzyme sequence was added to the 5' end and the 3' end thereof, was chemically synthesized and inserted into a multicloning site of the plasmid for preparing an adeno-associated virus vector.

Test Example 1: Measurement of Light-Induced Current in Cells Expressing p525, p548, and p550, Respectively, by Patch Clamp Method (Part 1)

With respect to the cells expressing p525, p548, and p550, respectively, after confirming the expression of venus under a microscope, measurement was performed using a patch clamp system (EPC-10, HEKA). As an extracellular solution, a solution composed of 138 mM NaCl, 3 mM KCl, 10 mM HEPES, 4 mM NaOH, 1 mM $CaCl_2$, and 2 mM $MgCl_2$ and adjusted to pH 7.4 with 1 N HCl was used. As a solution in the electrode, a solution composed of 130 mM CsCl, 1.1 mM EGTA, 2 mM $MgCl_2$, 0.1 mM $CaCl_2$, 10 mM NaCl, 10 mM HEPES, and 2 mM $Na_2ATP$ and adjusted to pH 7.2 with 1 N CsOH was used. The light irradiation (light source: LED) was performed for 1 second, and the light intensity was set to 1 $\mu W/mm^2$, the stimulus duration was set to 60 seconds, and the holding potential was set to −60 mV. The wavelength was set to each of 405, 455, 505, 560, 617, and 656 nm. The results are shown in FIG. 2. In FIG. 2, the measurement results for the cells expressing mVChR1 obtained in the same manner as the cells expressing p525, p548, and p550, respectively, are also shown. As apparent from FIG. 2, it was found that p525, p548, and p550 all have higher ion permeability than mVChR1.

Test Example 2: Measurement of Light-Induced Current in Cells Expressing p525 by Patch Clamp Method (Part 2)

When the light-induced current of p525 was measured in the same manner as in Test Example 1 except that the light irradiation was performed for 10 milliseconds, p525 had higher ion permeability than mVChR1.

Test Example 3: Measurement of Light-Induced Current in Cells Expressing p528 by Patch Clamp Method When the light-induced current of p528 was measured in the same manner as in Test Example 1, p528 had higher ion permeability than mVChR1.

Example 4: Modified Channelrhodopsin of Present Invention Composed of Amino Acid Sequence Represented by SEQ ID NO: 9 (Acquisition of Cells Expressing p578 (H172G))

The plasmid for preparing an adeno-associated virus vector expressing p548 prepared in Example 2 was subjected to site-specific mutagenesis using KOD mutagenesis kit (Code No. SMK-101, TOYOBO) according to its manual to substitute His at position 172 by Gly, whereby the plasmid for preparing an adeno-associated virus vector expressing p578 was prepared. Specifically, PCR was performed using a mutation primer (172G Forward Primer: GGACTGAGCAACCTGACCGGCCTGAA represented by SEQ ID NO: 21) at 10 pmol/µL and a reverse primer (GATCAGGATCACAGGACAGGTCAG represented by SEQ ID NO: 22) at 10 pmol/µL, and also using the plasmid for preparing an adeno-associated virus vector expressing p548 at 50 ng/µL as a template. The PCR reaction cycles were 5 cycles (1 cycle: 2 min at 94° C.→10 sec at 98° C.→7 min at 68° C.). By treating the PCR product with a restriction enzyme DpnI, the plasmid for preparing an adeno-associated virus vector expressing p548 used as the template was digested, and then, T4 Polynucleotide Kinase and Ligase were allowed to simultaneously act to circularize the linear plasmid by self-ligation, whereby the plasmid for preparing an adeno-associated virus vector expressing p578 was obtained. The cells expressing p578 were prepared in the same manner as in Example 1 except that the thus obtained plasmid for preparing an adeno-associated virus vector expressing p578 was used.

Example 5: Modified Channelrhodopsin of Present Invention Composed of Amino Acid Sequence Represented by SEQ ID NO: 10 (Acquisition of Cells Expressing p579 (H172a))

The plasmid for preparing an adeno-associated virus vector expressing p579 was prepared in the same manner as in Example 4 except that as a mutation primer, 172A Forward Primer: GCCCTGAGCAACCTGACCGGCCTGAA represented by SEQ ID NO: 23 was used, and the cells expressing p579 were prepared.

Example 6: Modified Channelrhodopsin of Present Invention Composed of Amino Acid Sequence Represented by SEQ ID NO: 11 (Acquisition of Cells Expressing p580 (H172K))

The plasmid for preparing an adeno-associated virus vector expressing p580 was prepared in the same manner as in Example 4 except that as a mutation primer, 172K Forward Primer: AAACTGAGCAACCTGACCGGCCTGAA represented by SEQ ID NO: 24 was used, and the cells expressing p580 were prepared.

Example 7: Modified Channelrhodopsin of Present Invention Composed of Amino Acid Sequence Represented by SEQ ID NO: 12 (Acquisition of Cells Expressing p581 (H172R))

The plasmid for preparing an adeno-associated virus vector expressing p581 was prepared in the same manner as in Example 4 except that as a mutation primer, 172R Forward Primer: CGCCTGAGCAACCTGACCGGCCTGAA represented by SEQ ID NO: 25 was used, and the cells expressing p581 were prepared.

Test Example 4: Measurement of Light-Induced Current in Cells Expressing p578, p579, p580, and p581, Respectively, by Patch Clamp Method The light-induced current in the respective cells was measured in the same manner as in Test Example 1. The results are shown in FIG. 3. In FIG. 3, the measurement results for the cells expressing p548 are also shown. As apparent from FIG. 3, p578, p579, p580, and p581 all had lower ion permeability than p548, but higher than mVChR1 (see FIG. 2 for the ion permeability of mVChR1).

Test Example 5: Measurement of τon and τoff of Cells Expressing p579 by Patch Clamp Method The τon and τoff were measured under the same conditions as for the measurement of the light-induced current in Test Example 4. The results are shown in FIG. 4 for τon, and in FIG. 5 for τoff. In each figure, the measurement results for the cells expressing p548 are also shown. As apparent from FIGS. 4 and 5, it was found that p579 in which His at position 172 in p548 was substituted by Ala shows τon and τoff both shorter than p548, and controls cells with a high time resolution.

Test Example 6: Introduction of p548 Gene into Retina Using Adeno-Associated Virus Vector and its Effect Experimental Method Preparation of Adeno-Associated Virus Vector The adeno-associated virus vector for introducing the p548 gene into the retina was prepared from three types of plasmids: the plasmid for preparing an adeno-associated virus vector expressing p548 prepared in Example 2, pAAV-RC, and pHelper using AAV Helper-Free System (Stratagene, La Jalla, CA) according to its manual. Specifically, to a tube after adding a solution of each plasmid (the amount of each plasmid was 15 μg) thereto and tapping, 1.5 mL of 0.3 M $CaCl_2$ was added, followed by stirring by inversion, and then, the content was added to 1.5 mL of 2×HBS (280 mM NaCl, 1.5 mM $Na_2HPO_4$, 50 mM HEPES, pH 7.1) provided in another tube. The resultant was again stirred by inversion, and then added dropwise to 293T cells cultured in a 15 cm culture dish to co-transfect the three types of plasmids by a calcium phosphate method, and the cells were cultured at 37° C. and 5% $CO_2$. After culturing for 3 days, the target virus particles were purified from the collected cells.

Experimental Animal

7-Month-old Royal College of Surgeons (RCS: rdy/rdy) rats were used. In RCS rats, the retina is once normally formed after birth, but photoreceptor cells start to degenerate from 3 weeks after birth and almost all photoreceptor cells disappear 3 months after birth, leading to visual loss. Therefore, in 7-month-old RCS rats, no visually evoked potential is recorded.

Introduction of p548 Gene into Retina

Under mixed anesthesia of ketamine (66 mg/kg) and xylazine (3.3 mg/kg), the bulbar conjunctiva of both eyes of each RCS rat was incised about 1 mm, a 32-gauge microsyringe was inserted through the pars plana, and 5 μL of a virus solution was injected into the vitreous body.

Measurement of Visually Evoked Potential

The visually evoked potential was measured 2 months after the virus solution was injected into the vitreous body of the RCS rat, and was recorded using an evoked response recorder (PuREC of Mayo Corporation). The electrodes for measuring the visually evoked potential were placed on the dura at positions of 6.8 mm from the bregma to the lambda on the median line and 3 mm left and right from the center in a state where the scalp was cut open to expose the cranium. The reference electrode was placed on the dura at a position of 12 mm from the bregma to the lambda on the median line. These electrodes placed were fixed using a dental cement. Under mixed anesthesia of ketamine (66 mg/kg) and xylazine (3.3 mg/kg), the measurement of the visually evoked potential was performed in a state where the pupils were dilated with 1 atropine and 2.5% phenylephrine hydrochloride. In the visual stimulation, various LEDs (stimulation light wavelength: 465, 525, and 650 nm) were used as light sources, and the stimulation was repeated 200 times at an irradiation time of 10 ms and a stimulation frequency of 1 Hz, and the visually evoked potential was recorded as an arithmetic mean.

Preparation of Retinal Flat-Mount Preparation and Retinal Section Preparation and Observation Thereof A retinal flat-mount preparation was prepared 8 months after the virus solution was injected into the vitreous body of the RCS rat for the purpose of confirming the expression of p548. The eyeball was extirpated and immediately thereafter fixed with a 4, paraformaldehyde solution, and then, the anterior eye segment was removed, and the neural retina was peeled from the choroid. The neural retina peeled from the choroid was flat-mounted on a microscope slide and observed under a fluorescence microscope to confirm the expression of p548 using venus as an index. Subsequently, the prepared retinal flat-mount preparation was embedded in an embedding agent for preparing a frozen tissue section (O.C.T. Compound of Sakura Finetek Japan Co., Ltd.) to prepare a frozen section (retinal section preparation), and the frozen section was observed under a fluorescence microscope to confirm the expression of p548 in the cross section of the retina using venus as an index.

Experimental Results

The measurement results of the visually evoked potential are shown in FIG. 6. As apparent from FIG. 6, by introducing the p548 gene into the retina, the visually evoked potential could be recorded at any of the stimulation light wavelengths of 465, 525, and 650 nm. The amplitude of the visually evoked potential was larger as the light intensity was stronger. A photograph of the retinal flat-mount preparation observed under a fluorescence microscope is shown in FIG. 7. As apparent from FIG. 7, the expression of p548 could be confirmed in the entire neural retina. Photographs of the retinal section preparation observed under a fluorescence microscope are shown in FIG. 8. As apparent from FIG. 8, the expression of p548 could be confirmed mainly in the retinal ganglion cell layer (the lower right photograph is the stained nucleus).

INDUSTRIAL APPLICABILITY

The present invention has industrial applicability in that it can provide a modified channelrhodopsin having high ion permeability (photoreactivity).

The invention claimed is:

1. A modified channelrhodopsin, which is a polypeptide obtained by substituting the third extracellular domain counted from the N-terminal side of three extracellular domains included in a Volvox carteri-derived channelrhodopsin by a corresponding extracellular domain of a *Chlamydomonas reinhardtii*-derived channelrhodopsin-2.

2. The modified channelrhodopsin according to claim 1, wherein the Volvox carteri-derived channelrhodopsin contains at least amino acids at positions 67 to 322 in the amino acid sequence represented by SEQ ID NO: 1.

3. The modified channelrhodopsin according to claim 2, which is obtained by substituting amino acids at positions 142 to 169 in the amino acid sequence represented by SEQ ID NO: 1 by amino acids at positions 143 to 170 in the amino acid sequence of a *Chlamydomonas reinhardtii*-derived channelrhodopsin-1 represented by SEQ ID NO: 2.

4. The modified channelrhodopsin according to claim 3, which is any of the following (a) to (c):
   (a) a polypeptide composed of the amino acid sequence represented by SEQ ID NO: 4;
   (b) a polypeptide that is composed of an amino acid sequence including deletion, substitution, addition, or insertion of one or a plurality of amino acids in the amino acid sequence represented by SEQ ID NO: 4, and that has a channelrhodopsin function; and
   (c) a polypeptide that is composed of an amino acid sequence having at least 90% sequence identity to the amino acid sequence represented by SEQ ID NO: 4, and that has a channelrhodopsin function.

5. The modified channelrhodopsin according to claim 4, which is a polypeptide composed of the amino acid sequence represented by SEQ ID NO: 8.

6. The modified channelrhodopsin according to claim 1, which is obtained by substituting the sixth transmembrane domain counted from the N-terminal side of seven transmembrane domains included in the Volvox carteri-derived channelrhodopsin by a corresponding transmembrane domain of a Chloromonas oogama-derived channelrhodopsin.

7. The modified channelrhodopsin according to claim 2, which is obtained by substituting amino acids at position 323 and downstream thereof in the amino acid sequence represented by SEQ ID NO: 1 by amino acids at position 265 and downstream thereof in the amino acid sequence of a Chloromonas oogama-derived channelrhodopsin represented by SEQ ID NO: 5.

8. The modified channelrhodopsin according to claim 6, which is any of the following (a) to (c):
   (a) a polypeptide composed of the amino acid sequence represented by SEQ ID NO: 6;
   (b) a polypeptide that is composed of an amino acid sequence including deletion, substitution, addition, or insertion of one or a plurality of amino acids in the amino acid sequence represented by SEQ ID NO: 6, and that has a channelrhodopsin function; and
   (c) a polypeptide that is composed of an amino acid sequence having at least 90% sequence identity to the amino acid sequence represented by SEQ ID NO: 6, and that has a channelrhodopsin function.

9. The modified channelrhodopsin according to claim 8, which is a polypeptide obtained by substituting His at position 172 in the polypeptide composed of the amino acid sequence represented by SEQ ID NO: 6 by another amino acid.

10. The modified channelrhodopsin according to claim 9, which is a polypeptide composed of the amino acid sequence represented by any of SEQ ID NOS: 9 to 12.

11. The modified channelrhodopsin according to claim 6, which is any of the following (a) to (c):
   (a) a polypeptide composed of the amino acid sequence represented by SEQ ID NO: 7;
   (b) a polypeptide that is composed of an amino acid sequence including deletion, substitution, addition, or insertion of one or a plurality of amino acids in the amino acid sequence represented by SEQ ID NO: 7, and that has a channelrhodopsin function; and
   (c) a polypeptide that is composed of an amino acid sequence having at least 90% sequence identity to the amino acid sequence represented by SEQ ID NO: 7, and that has a channelrhodopsin function.

12. A polynucleotide encoding the polypeptide according to claim 1.

13. An expression vector comprising the polynucleotide according to claim 12 functionally linked to a promoter.

14. A cell expressing the polypeptide according to claim 1.

15. The cell according to claim 14, wherein the cell is a neuron.

16. A method of production of a pharmaceutical for treating a subject suffering from damage to the outer retinal layers, comprising the step of formulating the polypeptide according to claim 1 with one or more pharmaceutically acceptable carriers.

17. The method according to claim 16, wherein the damage to the outer retinal layers is retinitis pigmentosa, age-related macular degeneration, or retinal detachment.

18. A pharmaceutical composition for treating damage to the outer retinal layers, comprising the polypeptide according to claim 1 as an active ingredient.

19. A method of production of a pharmaceutical for treating a subject suffering from damage to the outer retinal layers, comprising the step of formulating the polynucleotide according to claim 12 with one or more pharmaceutically acceptable carriers.

20. A method of production of a pharmaceutical for treating a subject suffering from damage to the outer retinal layers, comprising the step of formulating the expression vector according to claim 13 with one or more pharmaceutically acceptable carriers.

21. A pharmaceutical composition for treating damage to the outer retinal layers, comprising the expression vector according to claim 13 as an active ingredient.

* * * * *